(12) United States Patent
Kunio et al.

(10) Patent No.: US 12,076,118 B2
(45) Date of Patent: Sep. 3, 2024

(54) DEVICES, SYSTEMS, AND METHODS FOR DETECTING EXTERNAL ELASTIC LAMINA (EEL) FROM INTRAVASCULAR OCT IMAGES

(71) Applicant: Canon U.S.A., Inc., Melville, NY (US)

(72) Inventors: Mie Kunio, Yokohama (JP); Lampros Athanasiou, Medford, MA (US)

(73) Assignee: Canon U.S.A., Inc., Melville, NY (US)

( * ) Notice: Subject to any disclaimer, the term of this patent is extended or adjusted under 35 U.S.C. 154(b) by 510 days.

(21) Appl. No.: 17/492,376

(22) Filed: Oct. 1, 2021

(65) Prior Publication Data

US 2023/0108133 A1 Apr. 6, 2023

(51) Int. Cl.
 *A61B 5/00* (2006.01)
 *A61B 5/02* (2006.01)

(52) U.S. Cl.
 CPC ........ *A61B 5/02007* (2013.01); *A61B 5/6852* (2013.01); *A61B 5/742* (2013.01); *A61B 2560/0223* (2013.01)

(58) Field of Classification Search
 CPC .................................................. A61B 5/742
 See application file for complete search history.

(56) References Cited

U.S. PATENT DOCUMENTS

| | | | |
|---|---|---|---|
| 7,460,248 B2 | 12/2008 | Kurtz et al. |
| 7,843,572 B2 | 11/2010 | Tearney et al. |
| 7,847,949 B2 | 12/2010 | Tearney et al. |
| 7,865,231 B2 | 1/2011 | Tearney et al. |
| 7,872,759 B2 | 1/2011 | Tearney et al. |
| 7,889,348 B2 | 2/2011 | Tearney et al. |
| 7,982,879 B2 | 7/2011 | Desjardins et al. |
| 8,050,747 B2 | 11/2011 | Tearney et al. |
| 8,118,877 B2 | 2/2012 | Brauker et al. |
| 8,149,418 B2 | 4/2012 | Tearney et al. |

(Continued)

FOREIGN PATENT DOCUMENTS

WO 2020/159984 A1 8/2020

OTHER PUBLICATIONS

Irmina Gradus-Pizlo, et al., "Left Anterior Descending Coronary Artery Wall Thickness Measured by High-Frequency Transthoracic and Epicardial Echocardiography Includes Adventitia", Am J Cardiol, vol. 91, Jan. 2003, pp. 27-32.

(Continued)

*Primary Examiner* — Joseph M Santos Rodriguez
(74) *Attorney, Agent, or Firm* — Canon U.S.A., Inc. IP Division

(57) ABSTRACT

One or more devices, systems, methods and storage mediums for optical imaging medical devices, such as, but not limited to, Optical Coherence Tomography (OCT), single mode OCT, and/or multi-modal OCT apparatuses and systems, and methods and storage mediums for use with same, for detecting external elastic lamina (EEL) and/or lumen edge(s) are provided herein. One or more embodiments provide at least one method, device, apparatus, system, or storage medium to comprehend information, including, but not limited to, molecular structure of a vessel, and to provide an ability to manipulate the vessel information. In addition to controlling one or more imaging modalities, the EEL detection techniques may operate for one or more applications, including, but not limited to, manual or automatic EEL detection, stent positioning, stent selection, co-registration, and imaging.

20 Claims, 20 Drawing Sheets

(56) References Cited

U.S. PATENT DOCUMENTS

| | | |
|---|---|---|
| 8,150,496 B2 | 4/2012 | Tearney et al. |
| 8,172,757 B2 | 5/2012 | Jaffe et al. |
| 8,289,522 B2 | 10/2012 | Tearney et al. |
| 8,351,665 B2 | 1/2013 | Tearney et al. |
| 8,384,907 B2 | 2/2013 | Tearney et al. |
| 8,521,259 B2 | 8/2013 | Mandrusov et al. |
| 8,608,661 B1 | 12/2013 | Mandrusov et al. |
| 8,760,663 B2 | 6/2014 | Tearney et al. |
| 8,928,889 B2 | 1/2015 | Tearney et al. |
| 9,304,121 B2 | 4/2016 | Tearney et al. |
| 9,326,682 B2 | 5/2016 | Tearney et al. |
| 9,332,942 B2 | 5/2016 | Jaffer et al. |
| 9,498,114 B2 | 11/2016 | Friedman et al. |
| 9,513,276 B2 | 12/2016 | Tearney et al. |
| 9,526,656 B2 | 12/2016 | Serdarevic et al. |
| RE46,412 E | 5/2017 | Desjardins et al. |
| 9,931,171 B1 | 4/2018 | Peyman |
| 9,986,942 B2 | 6/2018 | Brauker et al. |
| 10,114,205 B2 | 10/2018 | Bukshtab et al. |
| 10,130,386 B2 | 11/2018 | Simpson et al. |
| 10,143,572 B2 | 12/2018 | Rapoza et al. |
| 10,238,281 B2 | 3/2019 | Isogai et al. |
| 10,241,028 B2 | 3/2019 | Rowe et al. |
| 10,264,963 B2 | 4/2019 | An et al. |
| 2004/0002650 A1 | 1/2004 | Mandrusov et al. |
| 2004/0162516 A1 | 8/2004 | Mandrusov et al. |
| 2006/0241495 A1 | 10/2006 | Kurtz |
| 2007/0233396 A1 | 10/2007 | Tearney et al. |
| 2007/0263226 A1 | 11/2007 | Kurtz et al. |
| 2009/0088648 A1 | 4/2009 | Jaffe et al. |
| 2010/0092389 A1 | 4/2010 | Jaffer |
| 2011/0149296 A1 | 6/2011 | Tearney et al. |
| 2012/0101374 A1 | 4/2012 | Tearney et al. |
| 2013/0100455 A1 | 4/2013 | Tearney et al. |
| 2014/0276059 A1 | 9/2014 | Sheehan |
| 2014/0323413 A1 | 10/2014 | Hageman et al. |
| 2015/0049339 A1 | 2/2015 | Tearney et al. |
| 2015/0230985 A1 | 8/2015 | Serdarevic et al. |
| 2016/0135832 A1 | 5/2016 | Simpson et al. |
| 2016/0228097 A1 | 8/2016 | Jaffer et al. |
| 2017/0238798 A1 | 8/2017 | Isogai et al. |
| 2017/0290514 A1 | 10/2017 | Liu et al. |
| 2018/0003481 A1 | 1/2018 | Yamada et al. |
| 2018/0025481 A1 | 1/2018 | Onimura et al. |
| 2018/0045501 A1 | 2/2018 | Elmaanaoui |
| 2018/0055953 A1 | 3/2018 | Jaffer et al. |
| 2018/0256024 A1 | 9/2018 | An et al. |
| 2018/0353077 A1 | 12/2018 | Strouthidis et al. |
| 2019/0008388 A1 | 1/2019 | Ando et al. |
| 2019/0159796 A1 | 5/2019 | Simpson et al. |
| 2019/0374109 A1 | 12/2019 | Wu et al. |
| 2019/0377134 A1 | 12/2019 | Yi et al. |
| 2020/0294659 A1 | 9/2020 | Gopinath et al. |
| 2020/0359911 A1 | 11/2020 | Olender et al. |

OTHER PUBLICATIONS

G. Rioufol, et al., "Adventitia measurement in coronary artery: an in vivo intravascular ultrasound study", Heart, Aug. 2006; vol. 92, Issue 7, pp. 985-986.

Michael J. A. Girad, et al., "Shadow Removal and Contrast Enhancement in Optical Coherence Tomography Images of the Human Optic Nerve Head", Investigative Opthalmology & Visual Science, Sep. 2011, vol. 52, Issue 10, pp. 7738-7748.

M. Félétou, "The Endothelium: Part 1: Multiple Functions of the Endothelial Cells—Focus on Endothelium-Derived Vasoactive Mediators", San Rafael (CA): Morgan & Claypool Life Sciences; Jul. 2011, doi: 10.4199/C00031ED1V01Y201105ISP019I; Accessible from: https://www.ncbi.nlm.nih.gov/books/NBK57145/ (PDF includes two pages).

Jean Martial Mari, et al., "Enhancement of Lamina Cribrosa Visibility in Optical Coherence Tomography Images Using Adaptive Compensation", Investigative Opthalmology & Visual Science, Mar. 2013, vol. 54, Issue 3, pp. 2238-2247.

Jing Chun Teo, et al., "Optimization of coronary optical coherence tomography imaging using the attenuation-compensated technique: a validation study", European Heart Journal—Cardiovascular Imaging, Jul. 2016, vol. 18, Issue 8, pp. 880-887.

Ziad A. Ali, et al., "Optical coherence tomography compared with intravascular ultrasound and with angiography to guide coronary stent implantation (Ilumien III: Optimize PCI): a randomised controlled trial", Lancet, Oct. 2016, vol. 388, Issue 10060, pp. 2618-2628 (13 pages in PDF).

Clinical trial information of "Ilumien IV: Optimal PCI" on ClinicalTrials.gov (https://clinicaltrials.gov/ct2/show/NCT03507777), Apr. 2018 (Last Update Posted: Jun. 11, 2021) (18 pages in PDF).

G. Tearney, et al., "Consensus Standards for Acquisition, Measurement, and Reporting of Intravascular Optical Coherence Tomography Studies: A Report From the International Working Group for Intravascular Optical Coherence Tomography Standardization and Validation," JACC, Mar. 2012; vol. 59, No. 12, pp. 1058-1072.

Chen, et al., "Quantitative 3D Analysis of Coronary Wall Morphology in Heart Transplant Patients: OCT-Assessed Cardiac Allograft Vasculopathy Progression", Med Image Anal., Dec. 2018; 50:95-105 (24 pages in PDF file).

Olender, et al., "A Mechanical Approach for Smooth Surface Fitting to Delineate Vessel Walls in Optical Coherence Tomography Images", IEEE Trans. on Med. Imaging, Jun. 2019; 38 (6): 1384-1397 (14 pages in PDF file).

Ali, Z. A., et al., "Intracoronary optical coherence tomography: state of the art and future directions", EuroIntervention, Jun. 2021, vol. 17, pp. e105-e123 (and 15 additional pages of supplementary data and supplementary figures 1-13).

Notification of Transmittal of, the International Search Report and Written Opinion of the International Searching Authority for PCT/US2022/077297, dated on Jan. 18, 2023 (including forms PCT/ISA/220, PCT/ISA/210, and PCT/ISA/237).

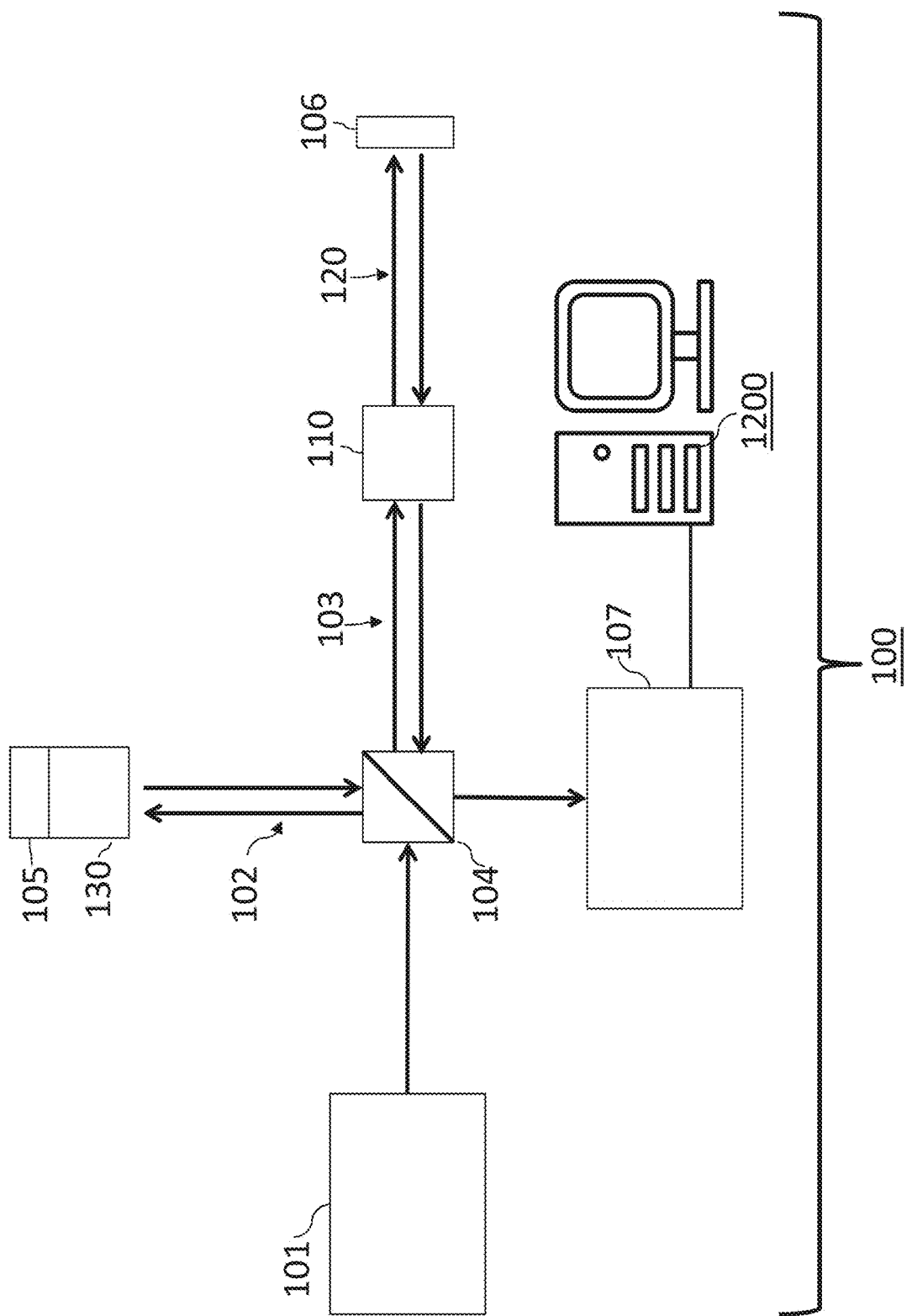

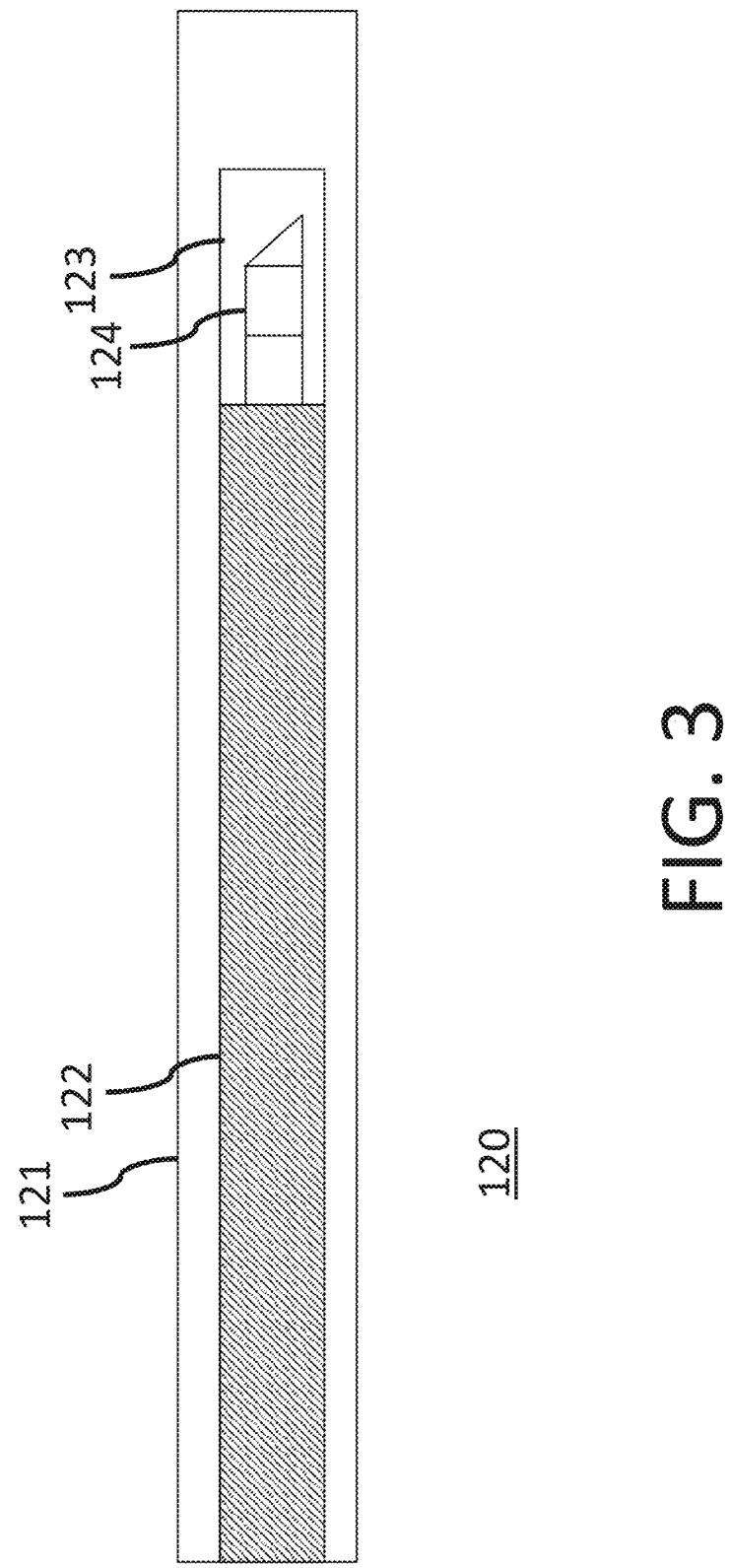

DEVICES, SYSTEMS, AND METHODS FOR DETECTING EXTERNAL ELASTIC LAMINA (EEL) FROM INTRAVASCULAR OCT IMAGES

FIELD OF THE INVENTION

This present disclosure generally relates to computer imaging and/or to the field of optical imaging, particularly to devices, systems, methods, and storage mediums for using multiple imaging modalities, such as, but not limited to, Optical Coherence Tomography (OCT), Multi-mode OCT (MMO-OCT), near-infrared fluorescence (NIRF), near-infrared auto-fluorescence (NIRAF), etc., for detecting external elastic lamina (EEL) from OCT image(s). Examples of OCT applications include imaging, evaluating and diagnosing biological objects, such as, but not limited to, for gastro-intestinal, cardio and/or ophthalmic applications, and being obtained via one or more optical instruments, such as, but not limited to, one or more optical probes, one or more catheters, one or more endoscopes, one or more capsules, and one or more needles (e.g., a biopsy needle). One or more devices, systems, methods and storage mediums for characterizing, examining and/or diagnosing, and/or measuring viscosity of, a sample or object in application(s) using an apparatus or system that uses and/or controls multiple imaging modalities are discussed herein.

BACKGROUND OF THE INVENTION

Optical coherence tomography (OCT) is a technique for obtaining high resolution cross-sectional images of tissues or materials, and enables real time visualization. The arm of the OCT techniques is to measure the time delay of light by using an interference optical system or interferometry, such as via Fourier Transform or Michelson interferometers. A light from a light source delivers and splits into a reference arm and a sample (or measurement) arm with a splitter (e.g., a beamsplitter). A reference beam is reflected from a reference mirror (partially reflecting or other reflecting element) in the reference arm while a sample beam is reflected or scattered from a sample in the sample arm. Both beams combine (or are recombined) at the splitter and generate interference patterns. The output of the interferometer is detected with one or more detectors, such as, but not limited to, photodiodes or multi-array cameras, in one or more devices, such as, but not limited to, a spectrometer (e.g., a Fourier Transform infrared spectrometer). The interference patterns are generated when the path length of the sample arm matches that of the reference arm to within the coherence length of the light source. By evaluating the output beam, a spectrum of an input radiation may be derived as a function of frequency. The frequency of the interference patterns corresponds to the distance between the sample arm and the reference arm. The higher frequencies are, the more the path length differences are.

During vascular diagnosis and intervention procedures, such as Percutaneous Coronary Intervention (PCI), users of optical coherence tomography (OCT) sometimes have difficulty understanding the tomography image in correlation with other modalities because of an overload of information, which causes confusion in image interpretation.

In one or more procedures, such as PCI, there is no algorithm or procedure to automatically detect EEL and to help physicians select a stent size, such as in PCI procedure. As such, there is a need to provide an automatic detection method to detect EEL and to help users select or set a stent size.

Accordingly, it would be desirable to provide at least one imaging or optical device, system, method, and storage medium for using, controlling, and/or emphasizing one or more imaging modalities and for automatically detecting EEL to help a user select a stent size.

SUMMARY OF THE INVENTION

Accordingly, it is abroad object of the present disclosure to provide imaging (e.g., OCT, NIRF, NIRAF, etc.) apparatuses, systems, methods and storage mediums for using and/or controlling one or more imaging modalities and for automatically detecting EEL to help a user select a stent size (e.g., diameter, length, diameter and length, wall area (e.g., an area between the EEL and a lumen, a user selected wall area, a predetermined wall area, an automatically selected wall area, etc.), etc.). It is also a broad object of the present disclosure to provide OCT devices, systems, methods and storage mediums using an interference optical system, such as an interferometer (e.g., SD-OCT, SS-OCT, etc.).

One or more embodiments provide at least one method, device, apparatus, system, or storage medium for automatically detecting EEL to help a user select a stent size (e.g., diameter, length, diameter and length, wall area (e.g., an area between the EEL and a lumen, a user selected wall area, a predetermined wall area, an automatically selected wall area, etc.), etc.).

In one or more procedures, one or more algorithms or methods discussed herein may be used to automatically detect EEL and to help and/or warn a user (e.g., a physician, technician, etc.) if a selected reference frame or frames are appropriate or inappropriate.

The present disclosure describes a means to allow OCT users to focus on the area of interest in all imaging modalities, such as, but not limited to, a tomography image, near-infrared auto-fluorescence (NIRAF) information in carpet view, near-infrared fluorescence (NIRF) information in carpet view, three-dimensional (3D) rendering of a coronary vessel in a half pipe display, lumen diameter display, longitudinal view, and angiography view. As described below, all of the displayed imaging modalities may be controlled by any one of several control bars which allow the user to change and update each display, synchronously, and to highlight NIRF and/or NIRAF data when appropriate. This allows the users to get a full view of the structural vessel information using multi-modalities and also allow configurability of the function for more targeted focus.

One or more embodiments of the present disclosure may be used in clinical application(s), such as, but not limited to, intervascular imaging, intravascular imaging, atherosclerotic plaque assessment, cardiac stent evaluation, intracoronary imaging using blood clearing, balloon sinuplasty, sinus stenting, arthroscopy, ophthalmology, ear research, veterinary use and research, etc.

In accordance with at least another aspect of the present disclosure, one or more technique(s) discussed herein may be employed as or along with features to reduce the cost of at least one of manufacture and maintenance of the one or more apparatuses, devices, systems and storage mediums by reducing or minimizing a number of optical and/or processing components and by virtue of the efficient techniques to cut down cost of use/manufacture of such apparatuses, devices, systems and storage mediums.

The following paragraphs describe certain explanatory embodiments. Other embodiments may include alternatives, equivalents, and modifications. Additionally, the explanatory embodiments may include several novel features, and a particular feature may not be essential to some embodiments of the devices, systems, and methods that are described herein.

According to other aspects of the present disclosure, one or more additional devices, one or more systems, one or more methods and one or more storage mediums using OCT and/or other imaging modality technique(s) are discussed herein. Further features of the present disclosure will in part be understandable and will in part be apparent from the following description and with reference to the attached drawings.

BRIEF DESCRIPTION OF THE DRAWINGS

For the purposes of illustrating various aspects of the disclosure, wherein like numerals indicate like elements, there are shown in the drawings simplified forms that may be employed, it being understood, however, that the disclosure is not limited by or to the precise arrangements and instrumentalities shown. To assist those of ordinary skill in the relevant art in making and using the subject matter hereof, reference is made to the appended drawings and figures, wherein:

FIG. 1A is a schematic diagram showing at least one embodiment of a system that may be used for detecting EEL in images in accordance with one or more aspects of the present disclosure;

FIG. 3 is a diagram of an embodiment of a catheter or probe that may be used with at least one embodiment of an apparatus, method, or system for performing EEL detection techniques in accordance with one or more aspects of the present disclosure;

DETAILED DESCRIPTION OF THE PRESENT INVENTION

Figure 1B:
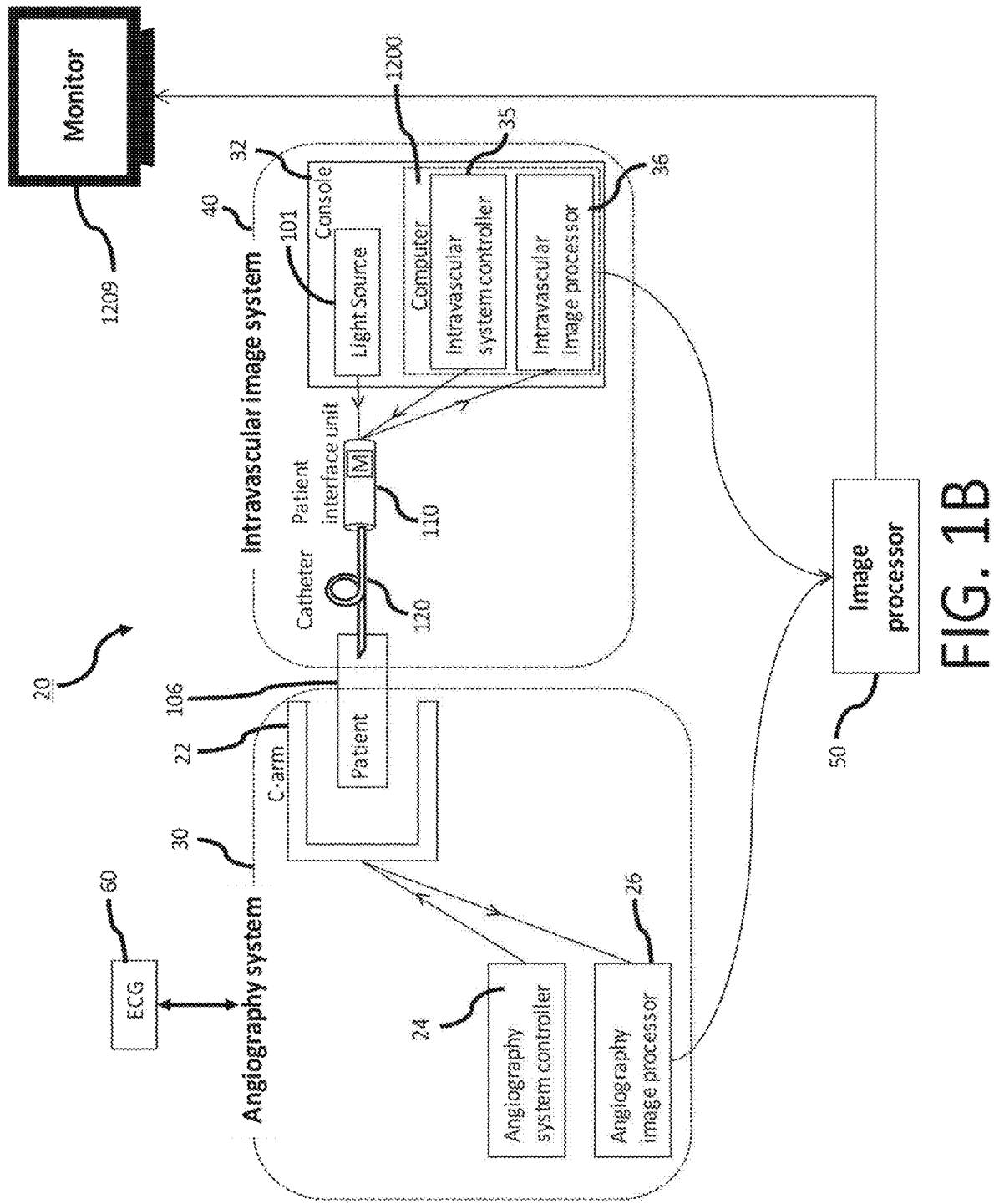
FIG. 1B shows a structure of at least one embodiment of a multimodality optical coherence tomography (MM-OCT) apparatus or system that may be used to detect EEL in accordance with one or more aspects of the present disclosure.

Embodiments will be described below with reference to the attached drawings. Like numbers refer to like elements throughout. It shall be noted that the following description is merely illustrative and exemplary in nature, and is in no way intended to limit the disclosure and its applications or uses. The relative arrangement of components and steps, numerical expressions and numerical values set forth in the embodiments do not limit the scope of the disclosure unless it is otherwise specifically stated. Techniques, methods, and devices which are well known by individuals skilled in the art may not have been discussed in detail since an individual skilled in the art would not need to know these details to enable the embodiments discussed below. Further, an endoscope as disclosed in the following which is used to inspect an inside a human body may also be used to inspect other objects. Examples of specialized endoscopes which are examples of endoscope in which an embodiment may be implemented including: angioscope; anoscope; arthroscope;

arterioscope; arthroscope, bronchoscope; capsule endoscope; choledochoscope; colonoscope; colposcope; cystoscope; encephaloscope; esophagogastroduodenoscope; esophagoscope; gastroscope; hysteroscope; laparoscope; laryngoscope; mediastinoscope; nephroscope; neuroendoscope; proctoscope; resectoscope; rhinoscope; sigmoidoscope; sinusoscope; thoracoscope; ureteroscope; uteroscope; borescope; fiberscope; inspection camera; and any specialized endoscope which may be adapted to include an embodiment. The endoscope may be flexible or rigid. An embodiment may also be a probe or an imaging apparatus.

One or more devices, optical systems, methods, and storage mediums for obtaining a direct image (e.g., black and white, color, etc.) of a subject, such as tissue, using an imaging function, feature, technique or method; a coregistration function, feature, technique, or method; and/or selecting an appropriate co-registration method, and/or for diagnosing, irrigating, suctioning, dilating (e.g., balloon), culturing, tissue sampling, performing a biopsy, implanting a drug and/or performing any other type of diagnosis and/or treatment using an imaging feature, function or technique are disclosed herein. In accordance with at least one aspect of the present disclosure, one or more devices, optical systems, methods, and storage mediums discussed herein use an imaging function, feature, technique or method; a coregistration function, feature, technique or method; selecting an appropriate co-registration method; and/or use an EEL detection method(s).

In one or more embodiments, multiple imaging modalities may be used to plan a procedure and confirm procedural success of percutaneous coronary intervention (PCI) in a catheterization laboratory at a hospital.

One or more devices, systems, methods and storage mediums for characterizing tissue, or an object or sample, using multiple imaging techniques or modalities (such as, but not limited to, OCT, NIRF, NIRAF, etc.) are disclosed herein. Several embodiments of the present disclosure, which may be carried out by the one or more embodiments of an apparatus, system, method and/or computer-readable storage medium of the present disclosure are described diagrammatically and visually in FIGS. 1A through 18.

Turning now to the details of the figures, FIG. 1A shows an OCT system 100 (as referred to herein as "system 100" or "the system 100") which operates to utilize an OCT technique, including, but not limited to, one or more embodiments of EEL detection techniques discussed herein, with optical probe applications in accordance with one or more aspects of the present disclosure. The system 100 comprises a light source 101, a reference arm 102, a sample arm 103, a splitter 104 (also referred to herein as a "beam splitter"), a reference mirror (also referred to herein as a "reference reflection") 105, and one or more detectors 107. The system 100 may include a phase shift device or unit 130, and, in one or more embodiments, the phase shift device or unit may be omitted. In one or more embodiments, the system 100 may include a patient interface device or unit ("PIU") 110 and a catheter 120 (as diagrammatically shown in FIGS. 1A-1B), and the system 100 may interact with a sample or target 106 (e.g., via the catheter 120 and/or the PIU 110). In one or more embodiments, the system 100 includes an interferometer, or an interferometer is defined by one or more components of the system 100, such as, but not limited to, at least the light source 101, the reference arm 102, the sample arm 103, the splitter 104 and the reference mirror 105.

The light source 101 operates to produce a light to the splitter 104, which splits the light from the light source 101 into a reference beam passing into the reference arm 102 and a sample beam passing into the sample arm 103. The beam splitter 104 is positioned or disposed at an angle to the reference mirror 105, the one or more detectors 107 and to the sample or target 106. The reference beam goes through the phase shift unit 130 (when included in a system, as shown in the system 100), and the reference beam is reflected from the reference mirror 105 in the reference arm 102 while the sample beam is reflected or scattered from a sample 106 through the PIU (patient interface unit) 110 and the catheter 120 in the sample arm 103. Both of the reference and sample beams combine (or recombine) at the splitter 104 and generate interference patterns. The output of the system 100 and/or the interferometer thereof is continuously acquired with the one or more detectors 107, e.g., such as, but not limited to, photodiodes or multi-array cameras. The one or more detectors 107 measure the interference or interference patterns between the two radiation or light beams that are combined or recombined. In one or more embodiments, the reference and sample beams have traveled different optical path lengths such that a fringe effect is created and is measurable by the one or more detectors 107. Electrical analog signals obtained from the output of the system 100 and/or the interferometer thereof are converted to digital signals to be analyzed with a computer, such as, but not limited to, the computer 1200, 1200' (shown in FIG. 17 or FIG. 18, respectively, discussed further below). In one or more embodiments, the light source 101 may be a radiation source or a broadband light source that radiates in a broad band of wavelengths. In one or more embodiments, a Fourier analyzer including software and electronics may be used to convert the electrical analog signals into an optical spectrum.

The light source 101 may include a plurality of light sources or may be a single light source. The light source 101 generates broadband laser lights in one or more embodiments. The light source 101 may include one or more of a laser, an organic Light-Emitting Diode (OLED), a Light-Emitting Diode (LED), a halogen lamp, an incandescent lamp, supercontinuum light source pumped by a laser, and/or a fluorescent lamp. The light source 101 may be any light source that provides light which can then be split up into at least three bands in which each band is further dispersed to provide light which is then used to for spectral encoding of spatial information. The light source 101 may be fiber coupled or may be free space coupled to the other components of the system or systems discussed herein, such as, but not limited to, the system 100, the system 100', the system 100", the system 100''', etc.

In accordance with at least one aspect of the present disclosure, a feature of OCT systems is implemented using fiber optics. As aforementioned, one application of an OCT technique of the present disclosure is to use OCT with a catheter 120 as schematically shown in FIGS. 1A-1B.

Referring now to FIG. 1B, shown is a schematic diagram of at least one embodiment of an imaging system 20 that may be used with one or more pullback embodiments and/or one or more EEL detection techniques discussed herein. The imaging system 20 may include an angiography system 30, an intravascular imaging system 40, an image processor 50, a display or monitor 1209, and an electrocardiography (ECG) device 60. The angiography system 30 includes an X-ray imaging device such as a C-arm 22 that is connected to an angiography system controller 24 and an angiography image processor 26 for acquiring angiography image frames of an object or patient 106.

The intravascular imaging system 40 of the imaging system 20 may include a console 32, a catheter 120 and a patient interface unit or PIU 110 that connects between the catheter 120 and the console 32 for acquiring intravascular image frames. The catheter 120 may be inserted into a blood vessel of the patient 106. The catheter 120 may function as a light irradiator and a data collection probe that is disposed in the lumen of a particular blood vessel, such as, for example, a coronary artery. The catheter 120 may include a probe tip, one or more radiopaque markers, an optical fiber, and a torque wire. The probe tip may include one or more data collection systems. The catheter 120 may be threaded in an artery of the patient 106 to obtain images of the coronary artery. The patient interface unit 110 may include a motor M inside to enable pullback of imaging optics during the acquisition of intravascular image frames. The imaging pullback procedure may obtain images of the blood vessel. The imaging pullback path may represent the co-registration path, which may be a region of interest or a targeted region of the vessel.

The console 32 may include a light source(s) 101 and a computer 1200. The computer 1200 may include features as discussed herein and below (see e.g., FIG. 1A, FIGS. 14-17, etc.), or alternatively may be a computer 1200' (see e.g., FIG. 18, etc.) or any other computer or processor discussed herein. In one or more embodiments, the computer 1200 may include an intravascular system controller 35 and an intravascular image processor 36. The intravascular system controller 35 and/or the intravascular image processor 36 may operate to control the motor M in the patient interface unit 110. The intravascular image processor 36 may also perform various steps for image processing and control the information to be displayed.

Various types of intravascular imaging systems may be used within the imaging system 20. The intravascular imaging system 40 is merely one example of an intravascular imaging system that may be used within the imaging system 20. Various types of intravascular imaging systems may be used, including, but not limited to, an OCT system, a multi-modality OCT system or an IVUS system, by way of example.

The imaging system 20 may also connect to an electrocardiography (ECG) device 60 for recording the electrical activity of the heart over a period of time using electrodes placed on the skin of the patient 106. The imaging system 20 may also include an image processor 50 for receiving angiography data, intravascular imaging data, and data from the ECG device 60 to execute various image-processing steps to transmit to a display 1209 for displaying an angiography image frame with a co-registration path. Although the image processor 50 associated with the imaging system 20 appears external to both the angiography system 30 and the intravascular imaging system 40 in FIG. 1B, the image processor 50 may be included within the angiography system 30, the intravascular imaging system 40, the display 1209 or a stand-alone device. Alternatively, the image processor 50 may not be required if the various image processing steps are executed using one or more of the angiography image processor 26, the intravascular image processor 36 of the imaging system 20, or any other processor discussed herein (e.g., computer 1200, computer 1200', etc.).

Figure 2A:
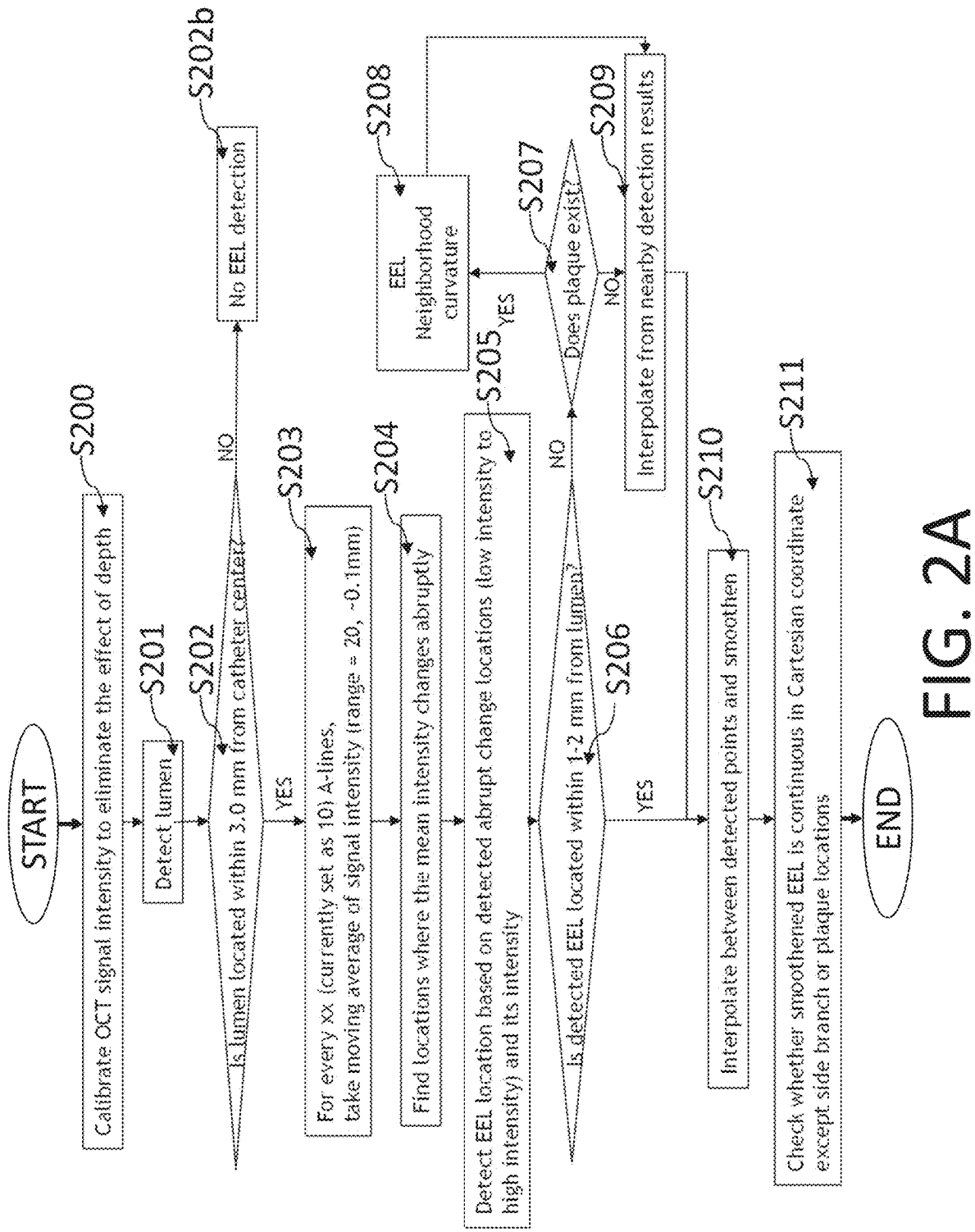
FIG. 2A is at least one embodiment of an EEL detection algorithm or method in accordance with one or more aspects of the present disclosure.
Figure 2B:
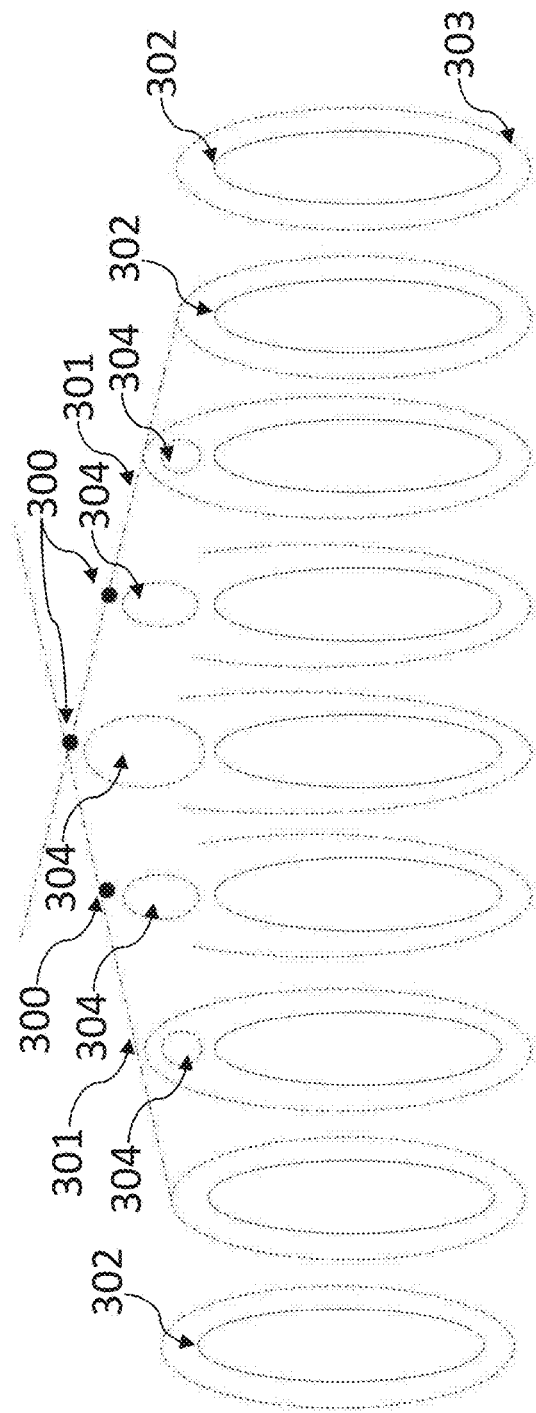
FIGS. 2B and 2C show at least one embodiment of an EEL pre neighborhood curvature and an EEL neighborhood curvature, respectively, that may be processed and/or obtained via one or more embodiments of an EEL detection algorithm or method in accordance with one or more aspects of the present disclosure.
Figure 2C:
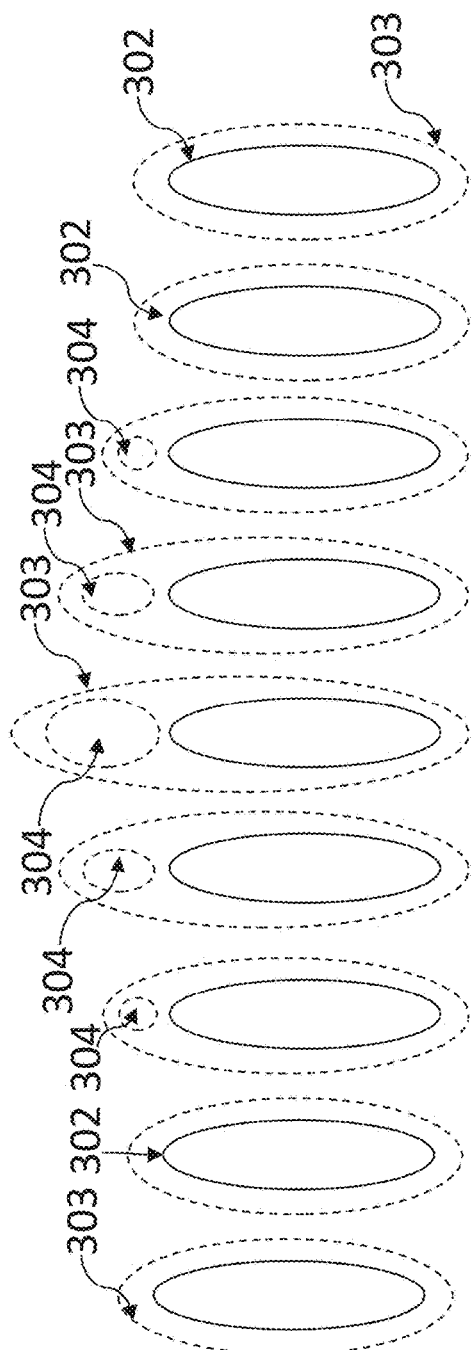

In one or more embodiments, one or more imaging modalities may be used to plan a procedure and confirm procedural success of percutaneous coronary intervention (PCI) in a catheterization laboratory at a hospital or may be used to plan and perform one or more other procedures, such as, but not limited to, imaging, EEL detection, etc. FIG. 2A shows at least one embodiment example of an overall workflow of EEL detection. In one or more embodiments, such a method may include the following steps: (i) calibrating an OCT signal intensity or other modality signal intensity to eliminate an effect of depth (see e.g., step S200 in FIG. 2A); (ii) detecting a lumen (see e.g., step S201 in FIG. 2A); (iii) determining whether the lumen is located within a predetermined distance (e.g., within 3.0 mm, within 2.0 mm, within 1.0 mm-3.0 mm, etc.) from a catheter center (see e.g., step S202 in FIG. 2A); (iv) if "Yes" in S202, taking a moving average of the signal intensity for a predetermined or set number, XX, of A-lines (e.g., 10 A-lines, 5 A-lines, 3 A-lines, 1-10 A-lines, 10 or more A-lines, 15 A-lines, a number of A-lines set by the user, etc.) (e.g., range=20, −0.1 mm) (see e.g., step S203 in FIG. 2A) and then proceeding to steps S204-S206 discussed below, or, if "No" in S202, then determining and/or indicating that no EEL detection occurred (see e.g., step S202b in FIG. 2A); (v) in step S204, finding locations where the mean intensity changes by a predetermined amount or changes abruptly (e.g., by 5 percent or more, by 10 percent or more, by 5-10% or more, an amount set or defined by the user, etc.) (see e.g., step S204 in FIG. 2A); (vi) detecting an EEL location based on the detected change or abrupt change locations (e.g., low intensity to high intensity) and an intensity of the EEL or of the detected change or abrupt change (see e.g., step S205 in FIG. 2A); (vii) determining whether the detected EEL location is within a predetermined distance (e.g., within 1 mm, within 2 mm, within 1-2 mm, within a distance set by a user, within a maximum penetration depth for one or more imaging modalities, within 1-2 mm for an OCT imaging modality, etc.) from a lumen (see e.g., step S206 in FIG. 2A); (viii) If "Yes" in S206, proceeding to steps S210 and S211 discussed below, or, if "No" in S206, proceeding to step S207; (ix) in step S207, determining whether plaque exists (see e.g., step S207 in FIG. 2A), and, if "Yes" in S207, (x) performing EEL neighborhood curvature processing (e.g., evaluating EEL pre neighborhood curvature and performing processing on same (as shown, for example, in FIG. 2B) to obtain or find the EEL neighborhood curvature (as shown for example, in FIG. 2C)) (see e.g., step S208 in FIG. 2A) and then proceed to steps S209-S211 discussed below, or, if "No" in S207, proceed to steps S209-S211 by (xi) interpolating from nearby detection results (see e.g., step S209 in FIG. 2A); (xii) interpolating between detected points and performing smoothening (see e.g., step S210 in FIG. 2A); and (xiii) checking whether the smoothened EEL is continuous in a Cartesian coordinate except side branch or plaque locations (see e.g., step S211 in FIG. 2A). As shown in FIGS. 2B-2C, in one or more embodiments where plaque is determined to be present or is located, the method may include the step of finding the EEL in pre neighborhood and/or neighborhood curvature frames and/or in plaque frames, and may create a line or lines (e.g., the neighborhood EEL curvature lines 301 as shown in FIG. 2B) from a top point of the detected EEL. Intermediate connection point(s) correspond(s) to a non-invisible plaque EEL point or points. For example, the top circles 304 in FIGS. 2B and 2C may correspond to plaque locations. In FIG. 2B, when the plaque 304 is present, the wall may be thick such that the EEL is not visible. In contrast, in FIG. 2B, in an area where the wall is not as thick or is thin/thinner, the EEL may be visible. Similarly, the non-invisible plaque EEL point(s) of the rest of the frames may be detected. In one or more embodiments, interpolation points 300 (as shown in FIG. 2B) may be used to create the neighborhood curvature line(s) 301. This step allows the method or algorithm to properly expand or find the EEL line 303 in one or more images (e.g., from FIG. 2B where the EEL 303 may not be fully displayed or accounted for to FIG. 2C where the EEL 303 is fully displayed). In this way, accurate image(s) or frame(s) may be obtained to distinguish between the lumen 302 and the EEL 303. In one or more embodiments, the method may determine EEL neighborhood curvature line(s) using any obtained EEL neighborhood curvature line frames (such as, but not limited to, EEL pre neighborhood curvature frames, EEL post neighborhood curvature frames, any combination of EEL neighborhood curvature frames, any combination of EEL pre neighborhood curvature frames and EEL post neighborhood curvature frames, any combination of EEL pre neighborhood curvature frames and any other kind of EEL neighborhood curvature frames, etc.).

Angiography shows a global view of coronary artery trees of a patient. Intravascular imaging modalities, such as intravascular ultrasound (IVUS), optical coherence tomography (OCT), and multimodality OCT (MM-OCT), may provide information in vessel walls by capturing cross-sectional views of the targeted coronary artery. In one or more embodiments, a method to select an appropriate method to coregister one or more intravascular images with one or more angiography images based on how at least one angiography image is acquired is described. Coregistration between an intravascular image and an angiography image may help physicians/practitioners connect information from different imaging modalities and understand one or more condition(s) of the patient.

In one or more embodiments of step S203, the number of A-lines to be analyzed may be set by a user or may be a predetermined number (or selected from a predetermined set of numbers). In at least one embodiment, the number of A-lines to be analyzed may be 10 A-lines, but the number of A-lines to be analyzed may depend on a total number of A-lines and available computational power. In one or more embodiments, the number of A-lines to be analyzed may be set by software or by the device or system using an algorithm or process as a default value, and/or a user may determine or set the number if preferred.

Additionally or alternatively, for step S203, one or more embodiments may determine or may be instructed with how many pixels may be grouped when taking the moving average. In one or more embodiments, 20 pixels may be set as a value, which corresponds to 0.1 mm or −0.1 mm. Since, in one or more embodiments, OCT penetration depth may be about 2-3 mm, and since one or more features to be detected may be located within 1-2 mm, a 0.1 mm or a −0.1 mm resolution may be used or may be reasonable. In one or more embodiments, a resolution may be set by a user depending on needs of the user and/or the procedure. If a user prefers, a user may determine the number of pixels that should be grouped when taking a moving average. Additionally or alternatively, in one or more embodiments, as a device or system obtains more data, the device or system may be able to learn or determine what the best number is on its own.

In one or more embodiments, such as for one or more embodiments of step S205, other features (e.g., other than abrupt intensity change from low intensity to high intensity) may be used to detect EEL. For example, in one or more embodiments, texture information of media or plaque types may be used. Calcified plaques are relatively easy to identify, and its feature may be enhanced by applying signal intensity calibration.

In one or more embodiments, since EEL may be located outside of media and plaques, if a user, device, or system may identify media and plaque features (even if EEL cannot be detected at 360 degree in Cartesian coordinate), EEL may be detected relatively accurately. One or more embodiments may detect EEL at 360 degree in Cartesian coordinate. Preferably, EEL is located outside of media and plaques. In one or more embodiments, EEL detection may be used with tissue type characterization, including plaque type characterization. If other algorithms or processes (e.g., deep learning, etc.) may identify different plaque types and media, then EEL detection may be performed more easily.

In one or more embodiments, using OCT (or other modality) signal compensation may result in increased visibility of a structure(s). In one or more embodiments, using smoothen A-line signal (moving average) may result in avoiding a sudden signal intensity change due to false features. In one or more embodiments, using polar and/or Cartesian coordinates may smoothen the detection curve and/or avoid meaningless detection. In one or more embodiments, utilizing lumen detection results may identify regions where EEL may not be detected.

In one or more embodiments, a threshold for an angle is preferably set. In one or more embodiments 360 degrees is set as an angle. In one or more embodiments where EEL may not be detected in 360 degree, an angle that is 180 degree visualization of EEL may be used as one of the thresholds. In one or more embodiments where ≥180 degree visualization of EEL is used as one of the thresholds for a particular clinical trial or trials, the angle threshold may be set to preferably be about 180 degrees or set at 180 degrees. In one or more embodiments, preferably the angle is no greater than 180 degrees (e.g., for a trial or procedure where one of the thresholds used is ≥180 degree visualization of EEL).

Preferably, in one or more embodiments, an EEL location may not be changed, or will not be changed, dramatically from frame to the next frame. In one or more embodiments where EEL location does not change dramatically from frame to the next frame, when EEL is not or cannot be detected in the frame that is currently processing, the software or the device or system using an algorithm or process may check a nearby frame or frames and determine whether EEL or part of the EEL may be detected in those frame(s). In a case where EEL may be detected in those frame(s), the original frame and the frame in which EEL may be detected may be registered via, e.g., lumen edge, and EEL location for the original frame may be determined. In one or more embodiments where an angle where EEL is not detected is small enough (e.g., the angle is less than 15 degrees, the angle is less than 10 degrees, the angle is less than 5 degrees, etc.), then the software or the process or algorithm may be interpolated in polar coordinate or in Cartesian coordinate.

In one or more embodiments, using a Cartesian coordinate may be helpful for EEL detection. Preferably, EEL may be a continuous path within a vessel in Cartesian coordinate. In one or more embodiments where the detected EEL contour is not continuous, the EEL contour may be modified to be continuous. In one or more embodiments where the detected EEL contour is not continuous, the EEL contour may be modified to be continuous, except for the existence of a side branch or plaque. In a case where a side branch or plaque exists, the EEL may be estimated by the EEL or parts of the EEL in the frames before the plaque has appeared.

In one or more embodiments, since a stent may not be usually placed where a side branch or plaque exists, using a Cartesian coordinate helps to (1) ensure the continuity of EEL, and (2) identify an inappropriate case(s) for EEL detection. For the second scenario of identifying an inappropriate case(s) for EEL detection, software or a device or system using an algorithm or process may still show the result to a user and ask the user whether the user wants to use that frame as a reference frame. In one or more embodiments, a lumen and/or a side branch may be detected within a range that OCT or other imaging modality may detect.

In one or more embodiments, the algorithm or process may determine how deep EEL may be located and/or how deep an EEL may be located. Since the reference frame (e.g., a reference frame for a PCI procedure) may be selected as the frame where the vessel looks normal, three (3) layers of the vessel (e.g., intima, media, and adventitia) may be visualized clearly. In such a situation using the intima, media, and adventitia layers, the EEL (the border between media and adventitia) may be located within 1-2 mm from the lumen surface.

In one or more embodiments, EEL detection may be an aid for PCI procedure, especially for stent sizing and navigating stenting location. Therefore, in a case where EEL may not be detected in a relatively shallow area from the lumen edge, the current frame may not be used as a reference frame, unless a user selects or sets that the current frame may be used as a reference frame by using the lumen edge for determining stent size (diameter).

FIG. 3 shows an embodiment of the catheter 120 including a sheath 121, a coil 122, a protector 123 and an optical probe 124. As shown schematically in FIGS. 1A-1B, the catheter 120 preferably is connected to the PIU 110 to spin the coil 122 with pullback (e.g., at least one embodiment of the PIU 110 operates to spin the coil 122 with pullback). The coil 122 delivers torque from a proximal end to a distal end thereof (e.g., via or by a rotational motor in the PIU 110). In one or more embodiments, the coil 122 is fixed with/to the optical probe 124 so that a distal tip of the optical probe 124 also spins to see an omnidirectional view of a biological organ, sample or material being evaluated, such as, but not limited to, hollow organs such as vessels, a heart, etc. For example, fiber optic catheters and endoscopes may reside in the sample arm (such as the sample arm 103 as shown in FIG. 1A) of an OCT interferometer in order to provide access to internal organs, such as intravascular images, gastro-intestinal tract or any other narrow area, that are difficult to access. As the beam of light through the optical probe 124 inside of the catheter 120 or endoscope is rotated across the surface of interest, cross-sectional images of one or more samples are obtained. In order to acquire three-dimensional data, the optical probe 124 is simultaneously translated longitudinally during the rotational spin resulting in a helical scanning pattern. This translation may be performed by pulling the tip of the probe 124 back towards the proximal end and therefore referred to as a pullback.

In one or more embodiments, the patient user interface 110 may comprise or include a connection component (or interface module), such as a rotary junction, to connect one or more components, such as one or more components of a probe (e.g., a catheter 120 (see e.g., FIGS. 1A-1B)), a needle, a capsule, a patient interface unit (e.g., the patient interface unit 110), etc., to one or more other components, such as, an optical component, a light source (e.g., the light source 101), a deflection section (e.g., such as the deflection or deflected section, which is a component that operates to deflect the light from the light source to the interference optical system, and then send light received from the interference optical system towards the at least one detector; a deflection or deflected section that includes at least one of: one or more interferometers, a circulator, a beam splitter, an isolator, a coupler, a fusion fiber coupler, a partially severed mirror with holes therein, and a partially severed mirror with a tap; etc.), the sample arm 102, a motor that operates to power the connection component and/or the patient user interface 110, etc. For example, when the connection member or interface module is a rotary junction, preferably the rotary junction operates as discussed below). In one or more other embodiments, the rotary junction may be at least one of: a contact rotary junction, a lenseless rotary junction, a lens-based rotary junction, or other rotary junction known to those skilled in the art.

In at least one embodiment, the PIU 110 may include a Fiber Optic Rotary Junction (FORJ), a rotational motor and translation motorized stage (e.g., a portion of the PIU 110), and a catheter connector (e.g., a portion of the PIU 110). The FORJ allows uninterrupted transmission of an optical signal while rotating a fiber along the fiber axis. The FORJ may have a free space optical beam combiner including a rotor and stator.

Descriptions of like-numbered elements present in the system 100' and already described above, such as for the system 100, shall not be repeated, and are incorporated by reference herein in their entireties.

In at least one embodiment, the console 1200, 1200' operates to control motions of a motor and translation motorized stage (hereinafter referred to as "motor" or "motor and stage"), acquires intensity data from the at least one detector(s) 107, and displays the scanned image (e.g., on a monitor or screen such as a display, screen or monitor 1209 as shown in the console 1200 of FIG. 17 and/or the console 1200' of FIG. 18 as further discussed below). In one or more embodiments, the console 1200, 1200' operates to change a speed of the motor and/or to stop the motor. The motor may be a stepping or a DC servo motor to control the speed and increase position accuracy.

In one or more embodiments, the console or computer 1200, 1200' operates to control the system 100 (and other systems, such as, but not limited to, the system 100', the system 100", the system 100'", etc. as discussed further below), the catheter 120 and/or one or more other above-described components of the system 100. In at least one embodiment, the console or computer 1200, 1200' operates to acquire intensity data from the at least one detector 107 of the OCT system/device/apparatus, and displays the image(s) (e.g., on a monitor or screen such as a display, screen or monitor 1209 as shown in the console 1200 of FIG. 17 and/or the console 1200' of FIG. 18 as further discussed below). The output of the one or more components of the system 100 (and other systems, such as, but not limited to, the system 100', the system 100", the system 100'", etc. as discussed further below) is acquired with the at least one detector 107 of the OCT system/device/apparatus, e.g., such as, but not limited to, photodiodes, Photomultiplier tube(s) (PMTs), line scan camera(s), or multi-array camera(s). Electrical analog signals obtained from the output of the system 100 (and/or other systems, such as, but not limited to, the system 100', the system 100", the system 100'", etc. as discussed further below) or one or more components thereof are converted to digital signals to be analyzed with a computer, such as, but not limited to, the computer 1200, 1200' (e.g., as shown in FIGS. 1A-1B and 14-17). In one or more embodiments, the light source 101 may be a radiation source or a broadband light source that radiates in a broad band of wavelengths. In one or more embodiments, a Fourier analyzer including software and electronics may be used to convert the electrical analog signals into an optical spectrum. In some embodiments, the at least one detector 107 comprises three detectors configured to detect three different bands of light.

One or more devices, optical systems, methods, and storage mediums for obtaining a direct image (e.g., black and white, color, etc.) of a subject, such as tissue, using an imaging function, feature, technique or method; a coregistration function, feature, technique, or method; and/or selecting an appropriate co-registration method, and/or for diagnosing, irrigating, suctioning, dilating (e.g., balloon), culturing, tissue sampling, performing a biopsy, implanting a drug and/or performing any other type of diagnosis and/or treatment using an imaging feature, function or technique are disclosed herein. In accordance with at least one aspect of the present disclosure, one or more devices, optical systems, methods, and storage mediums discussed herein use an imaging function, feature, technique or method; a coregistration function, feature, technique or method; and/or selecting an appropriate co-registration method.

Figure 4:
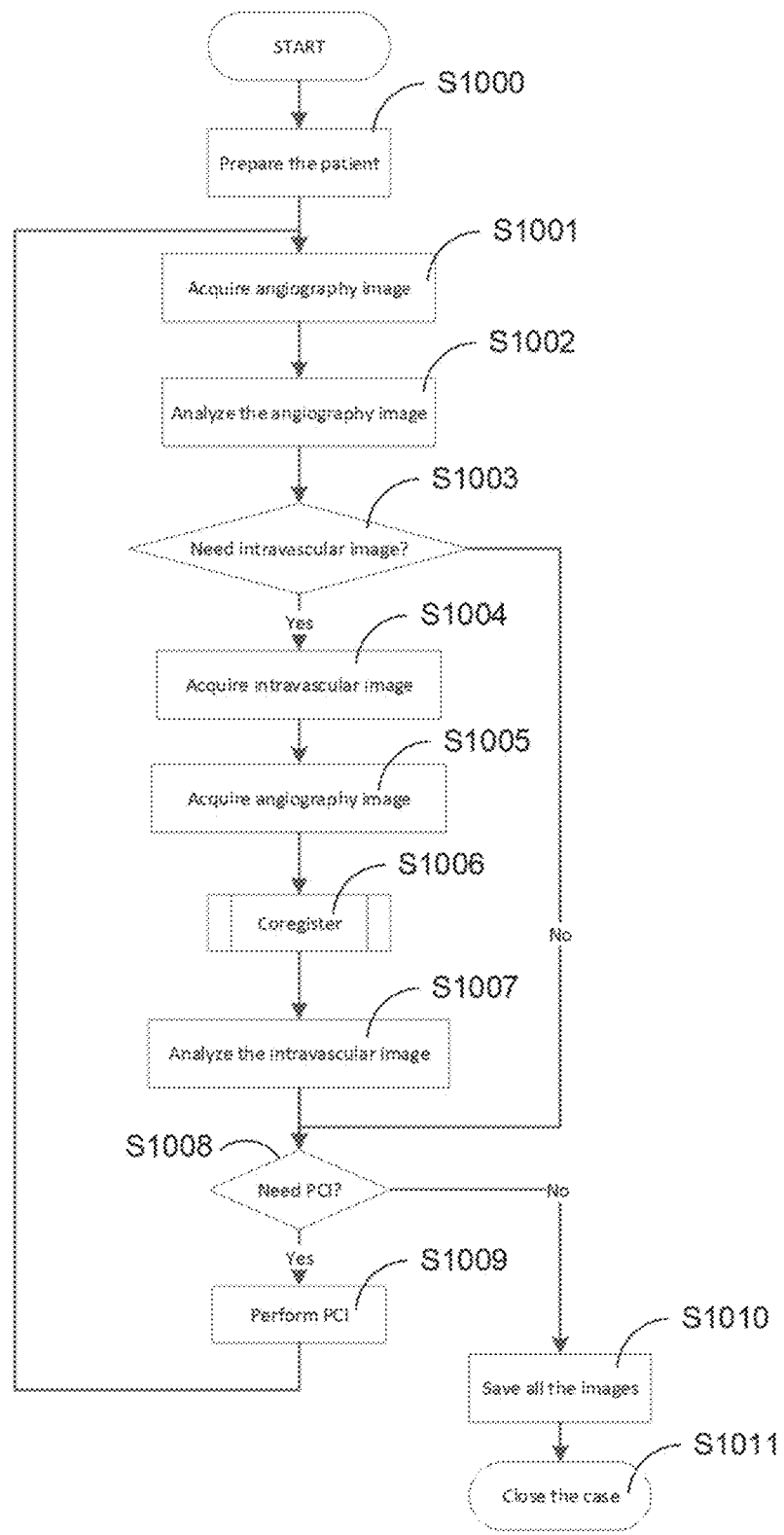
FIG. 4 shows at least one embodiment of an overall workflow in a catheterization laboratory that may be used with EEL detection in accordance with one or more aspects of the present disclosure.

In one or more embodiments, multiple imaging modalities may be used to plan a procedure and confirm procedural success of percutaneous coronary intervention (PCI) in a catheterization laboratory at a hospital. FIG. 4 shows at least one embodiment example of an overall workflow in a catheterization laboratory. In one or more embodiments, such a method may include the following steps: (i) preparing a patient (such as the patient 106 discussed above) (see e.g., step S1000 in FIG. 4); (ii) acquiring at least one angiography image (see e.g., step S1001 in FIG. 4); (iii) analyzing the angiography image (see e.g., step S1002 in FIG. 4); (iv) determining whether an intravascular image is needed (see e.g., step S1003 in FIG. 4), and, if "No", proceed to step S1008 discussed below, or, if "Yes", proceed to steps S1004-S1008; (v) if an intravascular image is needed in step S1003, then acquiring the intravascular image (see e.g., step S1004 in FIG. 4); (vi) acquiring the angiography image (see e.g., step S1005 in FIG. 4); (vii) performing coregistration (see e.g., step S1006 in FIG. 4; see also, FIG. 6 as discussed below); (viii) analyzing the intravascular image (see e.g., step S1007 in FIG. 4); (ix) determining whether PCI is needed (see e.g., step S1008 in FIG. 4), and, if "Yes", (x) perform the PCI (see e.g., step S1009 in FIG. 4) and then return to step S1001, or, if "No", (xii) saving all of the images (see e.g., step S1010 in FIG. 4) and then closing the case (see e.g., step S1011 in FIG. 4). Angiography shows a global view of coronary artery trees of a patient. Intravascular imaging modalities, such as intravascular ultrasound (IVUS), optical coherence tomography (OCT), and multi-modality OCT (MM-OCT), may provide information in vessel walls by capturing cross-sectional views of the targeted coronary artery. In one or more embodiments, a method to select an appropriate method to coregister one or more intravascular images with one or more angiography images based on how at least one angiography image is acquired is described. Coregistration between an intravascular image and an angiography image may help physicians/practitioners connect information from different imaging modalities and understand one or more condition(s) of the patient.

As shown in the flowchart of FIG. 2A, lumen edge detection may be done after OCT signal intensity calibration, before the calibration, or both (before and after the calibration). One or more embodiments may include the feature of calibrating the OCT (or other imaging modality) signal intensity to eliminate the effect of depth as aforementioned. One or more embodiments may include determining whether plaque exists and/or to check whether the smooth- ened EEL is continuous in Cartesian coordinate (except side branch or plaque locations). In one or more embodiments, the side branch or plaque locations may be considered to determine whether the EEL is continuous. In one or more embodiments, a determination is performed to detect whether a lumen is located within a predetermined distance from a portion of a catheter or from a catheter center, and, if "No", then no EEL detection occurs. One or more embodiments determine whether the EEL is located within a predetermined distance from the lumen as aforementioned, and, if "No", then a determination is performed to see whether plaque exists or not (if "No" to the latter determination, then interpolation is performed from nearby detection results).

Figure 5:
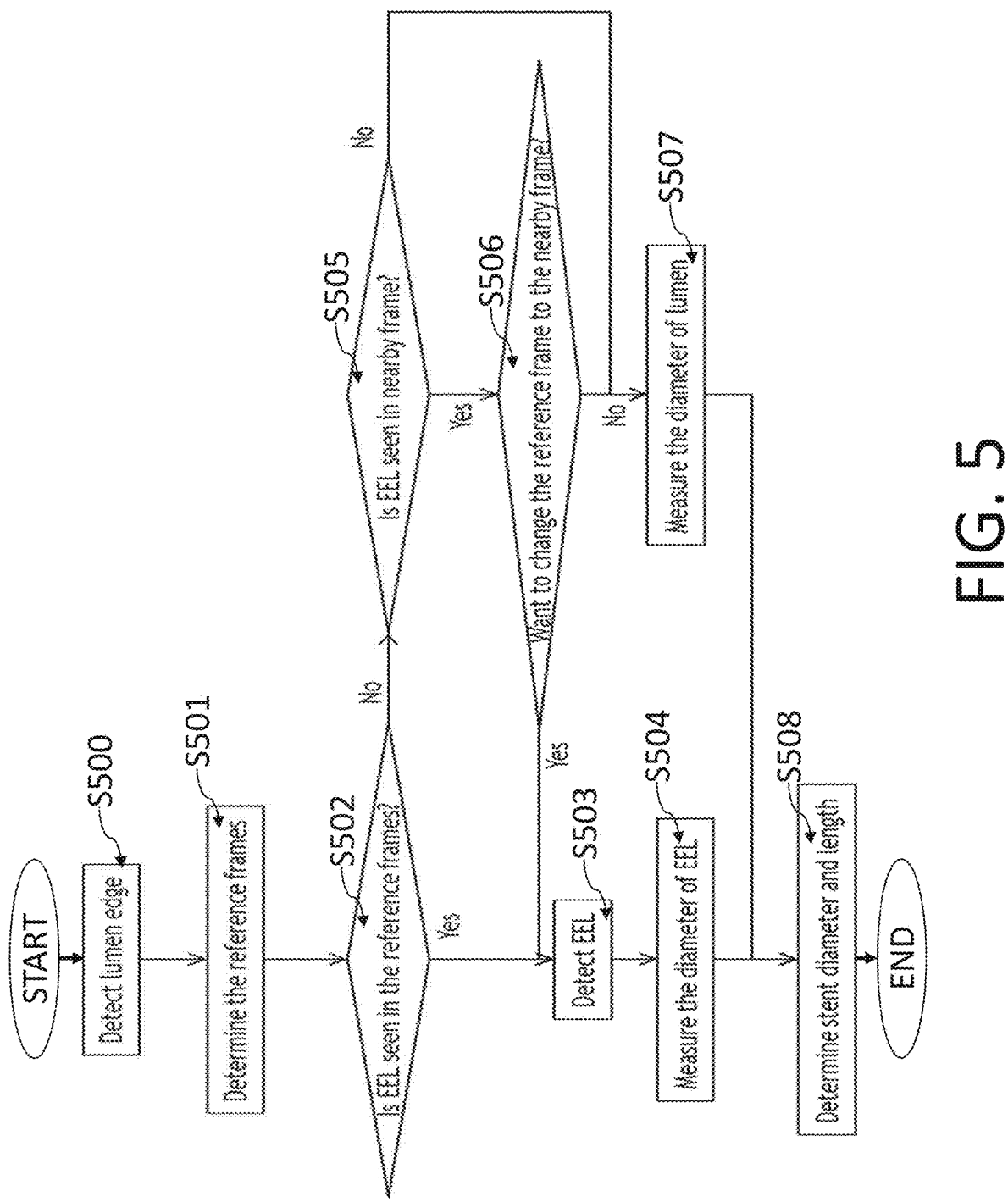
FIG. 5 is at least an additional embodiment of an EEL detection algorithm or method in accordance with one or more aspects of the present disclosure.

One or more embodiments of devices, systems, methods or algorithms discussed herein may analyze intravascular images. For instance, in at least one embodiment shown in FIG. 5, intravascular image(s) may be analyzed using one or more methods, and such method(s) may include the following steps: (i) detecting a lumen edge (see e.g., step S500 in FIG. 5); (ii) determining reference frame(s) (see e.g., step S501 in FIG. 5); (iii) determining whether an EEL is seen in the reference frame(s) (see e.g., step S502 in FIG. 5), and, if "Yes" in step S502, then proceeding to steps S503, S504, and S508 as shown in FIG. 5, or, if "No" in step S502, then proceeding to step S505 as shown in FIG. 5; (iv) in a case where an EEL is seen in the reference frame(s) ("Yes" in step S502 in FIG. 5), then detecting the EEL (see e.g., step S503 in FIG. 5), measuring the diameter of the EEL (see e.g., step S504 in FIG. 5), and determining stent diameter and length (see e.g., step S508 in FIG. 5); (v) in a case where an EEL is not seen in the reference frame(s) ("No" in step S502 in FIG. 5), then determining whether an EEL is seen in a nearby frame (e.g., a frame before or after the reference frame, a few frames away from the reference frame, a frame near to the reference frame, etc.) (see e.g., step S505 in FIG. 5), and, if "No" in step S505, then proceeding to step S507 in FIG. 5, or, if "Yes" in step S505, then proceeding to step S506 in FIG. 5; (vi) in step S506, determining whether to change the reference frame to a nearby frame (e.g., a frame before or after the reference frame, a few frames away from the reference frame, a frame near to the reference frame, etc.) (see e.g., step S506 in FIG. 5), and, if "Yes" in step S506 in FIG. 5, then proceeding to steps S503, S504, and S508, or, if "No" in step S506 in FIG. 5, then proceeding to step S507 in FIG. 5; (vii) in step S507, measuring the diameter of the lumen (see e.g., step S507 in FIG. 5); and (viii) determining the stent diameter and length (see e.g., step S508 in FIG. 5). In one or more embodiments, a good predictor for subsequent cardiac or acute cardiac events or for other analysis (manual or automatic) may be a wall area (e.g., an area between the EEL and a lumen, a user selected wall area, a predetermined wall area, an automatically selected wall area, etc.).

In one or more embodiments, user mark-ups may be used to aid or enhance the learning process. For example, a user may modify the EEL location detected automatically by software, the device(s), the system(s), the method(s), or the algorithm(s) discussed herein. In at least one embodiment for doing so, a graphical user interface (GUI) may have a button and/or guidance to navigate a user. This may be similar, or in addition to, lumen detection and its modification process(es). Once a user modifies the EEL location, the system(s), the device(s), the method(s), and/or the algorithm(s) may identify patterns in failed cases and may learn the patterns for future detection.

In one or more embodiments, the EEL may be automatically detected to help a user select a stent size and/or shape (e.g., stent diameter, stent length, stent circumference, stent volume, stent shape, etc.). With automatic detection of the EEL, the device(s), system(s), method(s), and/or algorithm(s) of the instant disclosure may be used to warn a user if a selected reference frame(s) is/are appropriate or not.

One or more embodiments of the subject disclosure may compensate signal intensity reduction due to depth and analyze the compensated intensity, so that one or more features located relatively deeper than a lumen surface may be enhanced for detection. As aforementioned, one or more embodiments may utilize one or both of polar coordinate and Cartesian coordinate information to create more realistic contour(s). In one or more embodiments, EEL contour(s) are preferably continuous. EEL contour(s) may be observed to be broken when plaque(s) exist and where the EEL is located too far from a lumen edge to be detected by OCT or other imaging modality/modalities. For usage in PCI procedure, EEL detection may be used to determine whether selected reference frame(s) is/are appropriate or not. If EEL cannot be detected or can be detected in less angles than it should be or preferably be, the device(s), system(s), method(s), and/or algorithm(s) may warn a user for potential inappropriate selection of the one or more reference frames. In or more embodiments, software may be used to warn the user for potential inappropriate selection of the one or more reference frames. One or more embodiments may utilize a lumen detection result to determine whether or not to detect an EEL. For example, in at least one embodiment, if a lumen is not detected within a 3 mm distance or other predetermined or set distance (e.g., 1 mm, 2 mm, 1-3 mm, any distance set by a user, a distance set by anatomy being imaged, a distance set or limited by anatomy, etc.) from a catheter center or other predetermined or set location in or around the catheter, then EEL may not be detected by the device, system, method, or algorithm or a warning or message may be issued to the user to not detect EEL or indicating that EEL will not be detected. In one or more embodiments, the EEL preferably may be located farther from a catheter compared to a lumen location.

Figure 6:
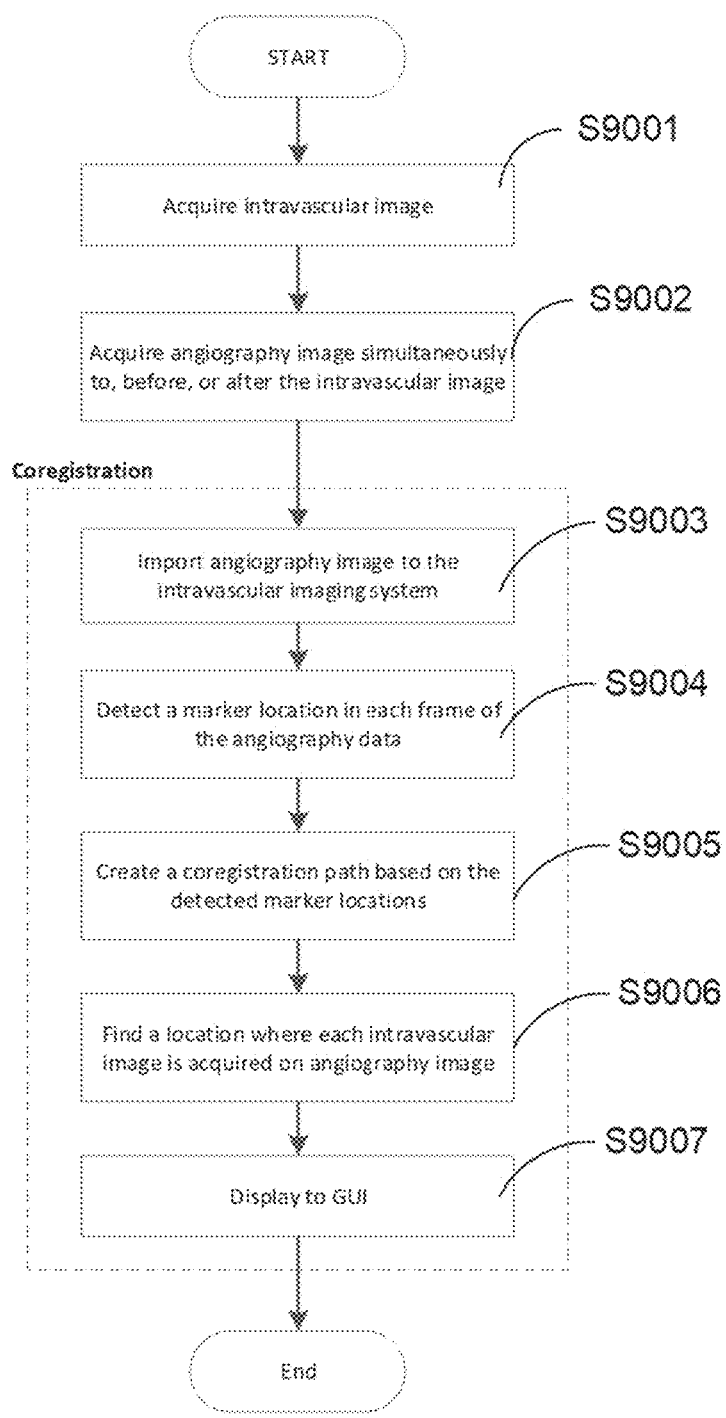
FIG. 6 shows at least one embodiment of an overall workflow of coregistration in accordance with one or more aspects of the present disclosure.

FIG. 6 describes an embodiment of an overall workflow of coregistration (e.g., an embodiment example of one or more steps of the "Coregister" subprocess box step S1006 shown in FIG. 4). In one or more embodiments, a method may include acquiring an intravascular image (see e.g., step S9001 in FIG. 6), and may include acquiring an angiography image simultaneously to, before, or after the intravascular image (see e.g., step S9002 in FIG. 6). The detailed workflow of the first 3 steps of coregistration (import angiography image (see e.g., step S9003 in FIG. 6), detect a marker location (see e.g., step S9004 in FIG. 6), and create a coregistration path (see e.g., step S9005 in FIG. 6) are discussed further below. Since an imaging catheter path may be used as a coregistration path, the accuracy of coregistration may depend on the accuracy of an imaging catheter path generation. After importing an angiography image to the system (see e.g., step S9003 in FIG. 6), the system checks whether the cardiac phase information is associated with the imported angiography image. If so, the system checks whether the imported angiography image has enough or a sufficient number of frames (e.g., above a predetermined number or threshold, available for a predetermined amount of time, etc.) without the contrast media in the predetermined area (e.g., the targeted vessel (i.e., the vessel region where the intravascular image is acquired)). The one or more criterion for the number of frames may be determined in relation to a cardiac cycle. The system or device judges that the number of frames is sufficient if (or in a case where) the angiography frames without the contrast media are available for at least one cardiac cycle. This checking process may be assisted by a user as needed. Based on these two pieces of information (i.e., the availability of cardiac phase information and the availability of a number of angiography frames without the contrast media), the system may automatically select either of the following processes of a coregistration path generation.

One or more embodiments may involve a case when the angiography image has the cardiac phase information (e.g., the angiography data is synchronized with an ECG signal) and when there is enough or a sufficient number of angiography frames without the contrast media in the predetermined area (e.g., the targeted vessel). In this case, the system may directly detect a coregistration path (e.g., an imaging catheter path). Detection accuracy may be improved by the effect of cardiac motion with the usage of the cardiac phase information and by checking the detected imaging catheter path location with the detected marker location. One or more embodiments may involve a case when the angiography image does not have the cardiac phase information and/or when there is not enough or a sufficient number of angiography frames without the contrast media in the targeted vessel. In this case, a coregistration path (e.g., an imaging catheter path) is hard to be detected directly from each angiography frame. Therefore, the system generates the coregistration path or imaging catheter path accurately by using the detected marker location. In one or more embodiments, a coregistration method may include finding a location where each intravascular image is acquired on an angiography image (see e.g., step S9006 in FIG. 6), and may include displaying information (such as the location) to a GUI (see e.g., step S9007 in FIG. 6).

In one or more embodiments, the acquired and/or imported angiography frames are preferably split into two groups by selecting each frame for evaluation: (1) the frame without the contrast media in the targeted vessel (the frames that are captured before the contrast media reached to the intravascular imaging region), and (2) the frame with the contrast media in the targeted vessel. Then, an imaging catheter path may be detected from each angiography frame in Group (1), and vessel contours and a radiopaque marker on the imaging catheter may be detected from each angiography frame in Group (2). As an example, a guidewire over which the imaging catheter is delivered to the targeted vessel or a drive-cable of the imaging catheter may be used as the imaging catheter path. The imaging catheter path and the vessel contours can be detected by applying an edge detection filter, such as Sobel, Canny, Prewitt, Roberts, Kernel, Laplacian of Gaussian, or others, and/or any combination from these. The radiopaque marker can be detected with, for example, Viterbi-based method, and/or any machine learning or deep learning-based method. The detected information is saved to each angiography frame with the cardiac phase information. The cardiac phase information may be obtained based on an ECG signal. One way to evaluate the cardiac phase information is calculating the percentage of cardiac cycle length. After the processes of detecting and saving for entire angiography frames (e.g., selecting a first frame, determining whether a contrast media is in a target (e.g., a targeted vessel), detecting an intravascular imaging catheter path in a case with no contrast media, saving the information of the detected catheter path and its cardiac phase with the frame in a case with no contrast media, detecting a vessel contour of a targeted region and marker in a case with contrast media, saving the information of the detected vessel contour, marker, and its cardiac phase with the frame in the case with contrast media, checking whether the evaluated frame is the last frame or not, moving to the next frame in a case where the evaluated frame is not the last frame, etc.), the system or device may choose one angiography frame from Group (2) and finds an angiography frame with the same cardiac phase in Group (1). Then, the imaging catheter path detected in the angiography frame selected from Group (1) may be overlaid on the angiography frame selected from Group (2). Using this overlaid image, the system or device may determine or evaluate whether the detected marker is located or is disposed on or within a certain distance from the detected imaging catheter path (see e.g., one or more of: determining whether a detected catheter path is located within a detected vessel contour; determining whether the detected marker location is on the catheter path in a case where the detected catheter path is located within the detected vessel contour; determining whether the detected marker location is close enough to the catheter path in a case where the detected marker location is not on the catheter path; determining whether there is another frame without contrast media at the same cardiac phase in a case where the detected marker location is not close enough to the catheter path and, if so, return to overlaying the selected frames or, if not, proceed to determining whether the frame with contrast media is the last frame; or in a case where the detected marker location is close enough to the catheter path, then proceed to find a closest point on the catheter path and update the marker location and then proceed to save the information of the catheter path location with the selected angiography frame with contrast media, as well as the detected/updated marker location; or in a case where the detected marker location is on the catheter path in the step of determining whether the detected marker is located on the catheter path, then proceed directly to the saving step). The threshold of the distance may be pre-determined by the system or determined by a user. If the overlaid image meets both criteria, the information of the detected catheter path location is saved with the angiography frame selected from Group (2). When the detected marker is not located or disposed on the detected imaging catheter path but is located or disposed within a certain distance, the closest location to the detected marker location on the imaging catheter path is searched, and its location is saved with the angiography frame selected from Group (2) by updating the detected marker location. The system may also check whether the detected imaging catheter path is located or disposed between or within the detected vessel contours to make sure the detected imaging catheter path may be a representative line of the vessel's longitudinal direction. If the overlaid image does not meet either one of the criteria, the system searches another angiography frame in Group (1) and follows the same processes. If there is no other angiography frame in Group (1) with the same cardiac phase, the system stops the processes for the angiography frame selected from Group (2). Then, the system selects another frame in Group (2) and repeats the entire set of processes until the last frame in Group (2) is processed. Indeed, at least this embodiment and other embodiments for performing co-registration may be used as discussed in PCT/US2020/015403, filed Jan. 28, 2020, the entirety of which is incorporated by reference herein, and as discussed in U.S. Pat. App. No. 62/798,885, filed on Jan. 30, 2019, the entirety of which is incorporated by reference herein.

In accordance with at least one aspect of the present disclosure and as aforementioned, one or more additional methods for lumen, stent, and/or artifacts detection of OCT images, or images of other imaging modalities, are provided herein, or may be used with one or more of the features or aspects of the present disclosure, and are discussed in U.S. patent application Ser. No. 16/414,222, filed on May 16, 2019 and published on Dec. 12, 2019 as U.S. Pat. Pub. No. 2019/0374109, the entire disclosure of which is incorporated by reference herein in its entirety.

A computer, such as the console or computer 1200, 1200', may perform any of the aforementioned steps (e.g., of FIGS. 2A-2C; of FIG. 4; of FIG. 5; of FIG. 6; etc.) for any system being manufactured or used, including, but not limited to, system 100, system 100', system 100", system 100''', etc.

Figure 7A:
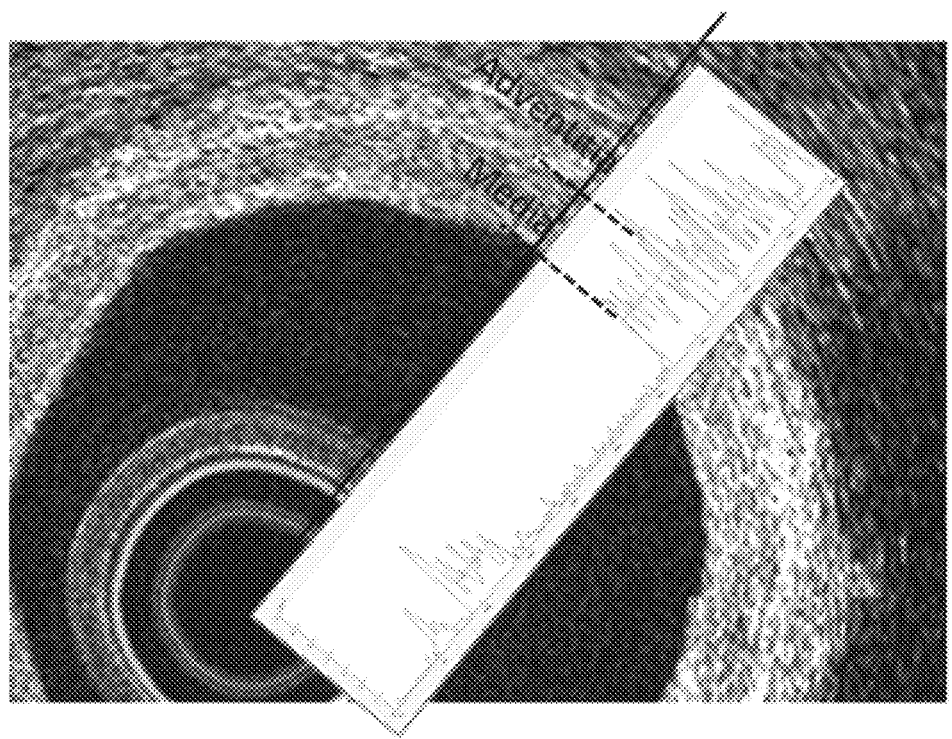
FIGS. 7A-7B show at least one embodiment of detecting an abrupt signal change and EEL location in accordance with one or more aspects of the present disclosure.
Figure 7B:
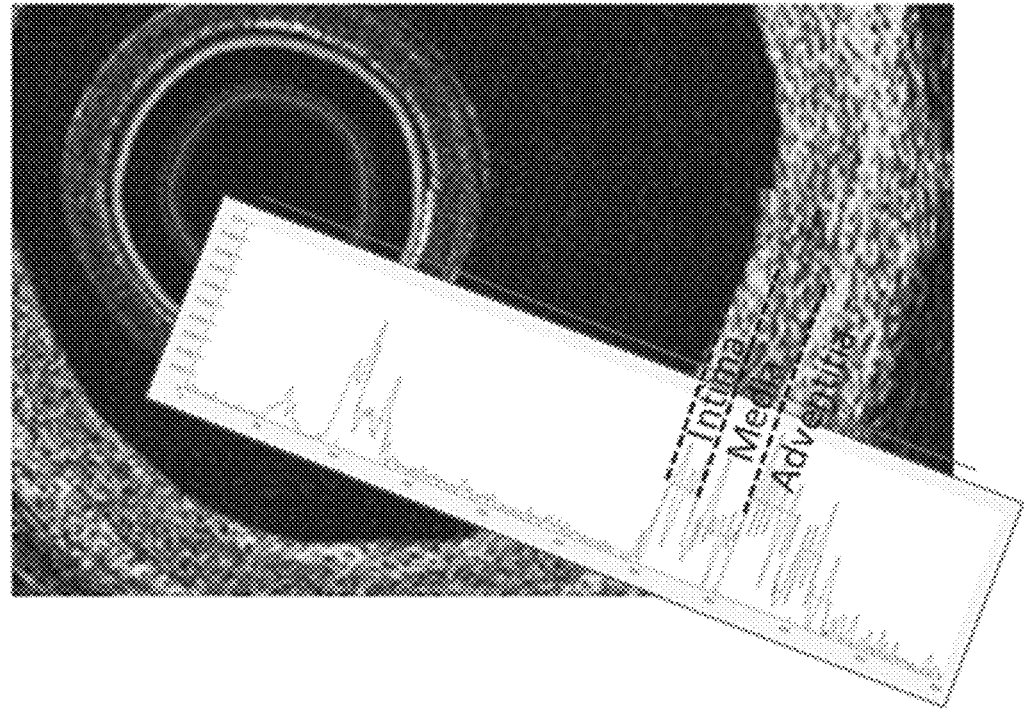

FIGS. 7A-7B show at least one embodiment example of detecting an abrupt signal intensity change and EEL location. Based on various signal intensity changes as shown in FIGS. 7A and 7B, a device, system, method, or algorithm may detect layers as well, such as, but not limited to, Intima, Media, and Aventitia (see e.g., FIG. 7A for Adventitia and Media detection and see e.g., FIG. 7B for Intima, Media, and Aventitia detection).

Figure 8B:
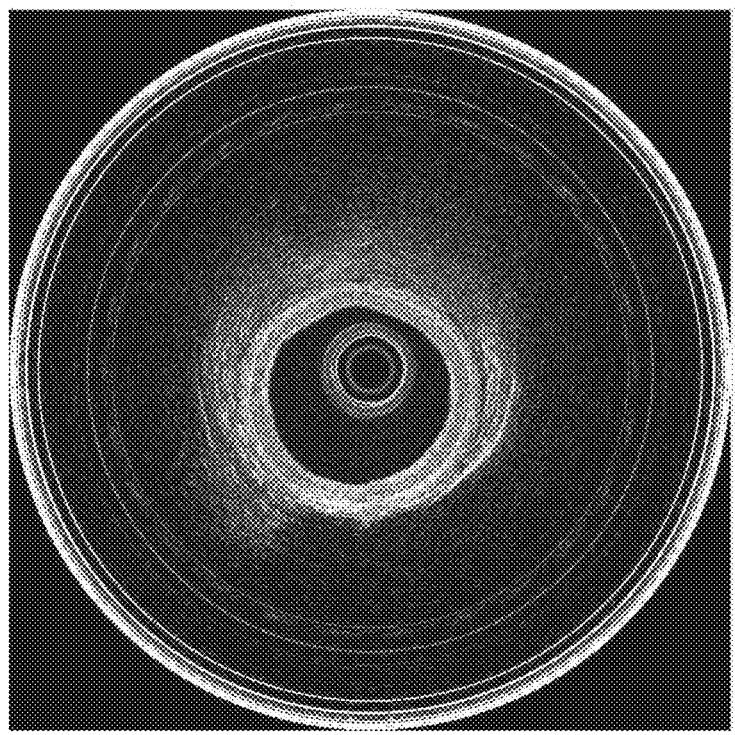
FIG. 8A and FIG. 8B show at least one embodiment of an original image frame and a compensated image frame, respectively, in accordance with one or more aspects of the present disclosure.
Figure 8A:
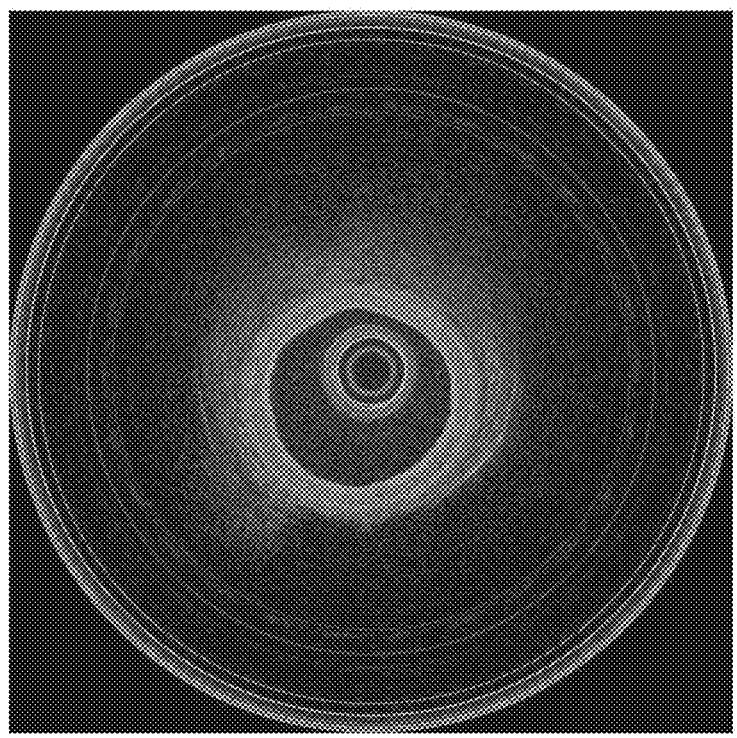

FIGS. 8A and 8B show at least one embodiment example of an original frame and a compensated frame, respectively. FIGS. 8A and 8B show frame 334 of an experiment conducted.

Figure 9:
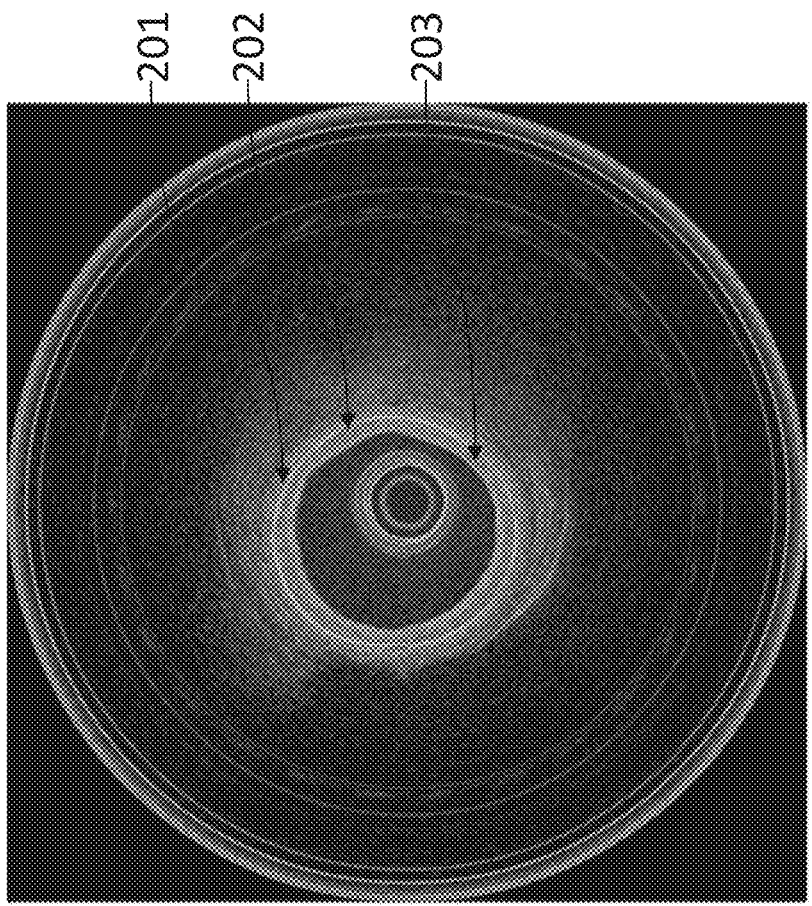
FIG. 9 shows at least one embodiment of using a ground truth data, data from the original image of FIG. 8A, and data from the compensated image of FIG. 8B as well as corresponding RMSE, max and min values in accordance with one or more aspects of the present disclosure.

FIG. 9 shows at least one embodiment of using a ground truth data (201 in FIG. 9), data from the original image (203 in FIG. 9) of FIG. 8A, and data from the compensated image (202 in FIG. 9) of FIG. 8B as well as corresponding RMSE, max, and min values. As shown in FIG. 9, the compensated data had an RMSE value of 0.0197, Max value of 0.0446 mm, and Min value of $5.64 \times 10-5$ mm. The original data had an RMSE value of 0.104 mm, a Max value of 0.191 mm, and a Min value of $8.73 \times 10-4$ mm.

Figure 10B:
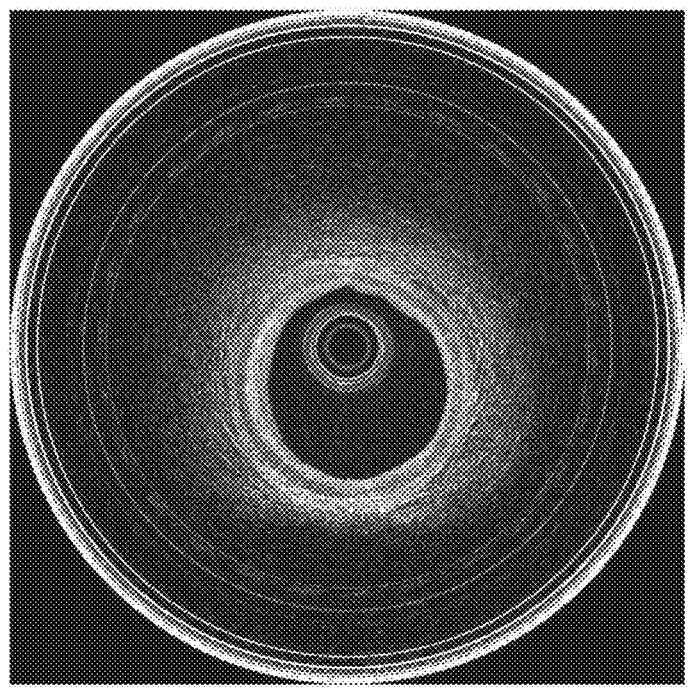
FIG. 10A and FIG. 10B show at least another embodiment of an original image frame and a compensated image frame, respectively, in accordance with one or more aspects of the present disclosure.
Figure 10A:
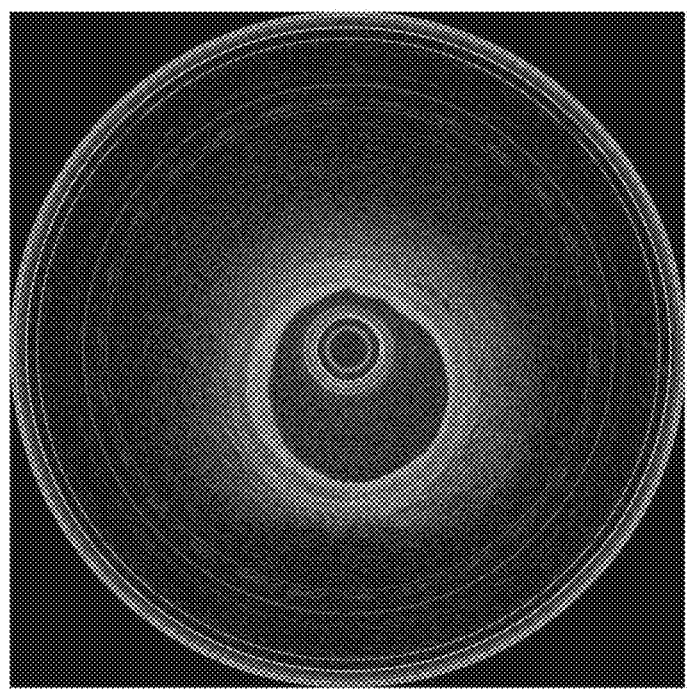

FIG. 10A and FIG. 10B show at least another embodiment of an original image frame and a compensated image frame, respectively. FIGS. 10A and 10B show frame 560 of the conducted experiment.

Figure 11:
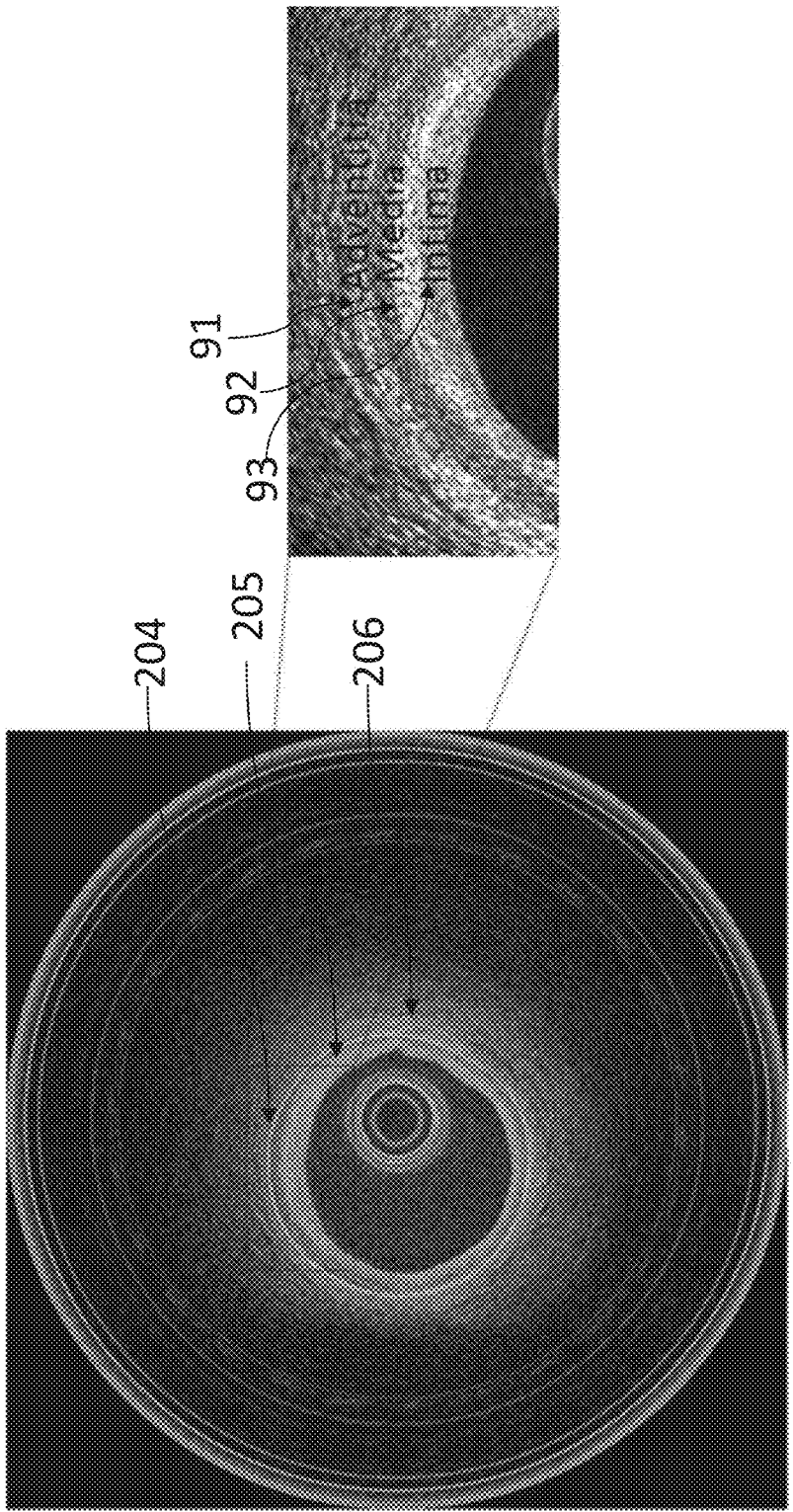
FIG. 11 shows at least one embodiment of using a ground truth data, data from the original image of FIG. 10A, and data from the compensated image of FIG. 10B as well as corresponding RMSE, max and min values in accordance with one or more aspects of the present disclosure.

FIG. 11 shows at least one embodiment of using a ground truth data (204 in FIG. 11), data from the original image (206 in FIG. 11) of FIG. 10A, and data from the compensated image (205 in FIG. 11) of FIG. 10B as well as corresponding RMSE, max, and min values. As shown in FIG. 11, the compensated data had an RMSE value of 0.120 mm, Max value of 0.246 mm, and Min value of $1.37 \times 10-7$ mm. The original data had an RMSE value of 0.235 mm, a Max value of 0.609 mm, and a Min value of $5.48 \times 10-4$ mm. The Adventitia 91, the Media 92, and the Intima 93 detection results are shown on the right side of FIG. 11.

Figure 12B:
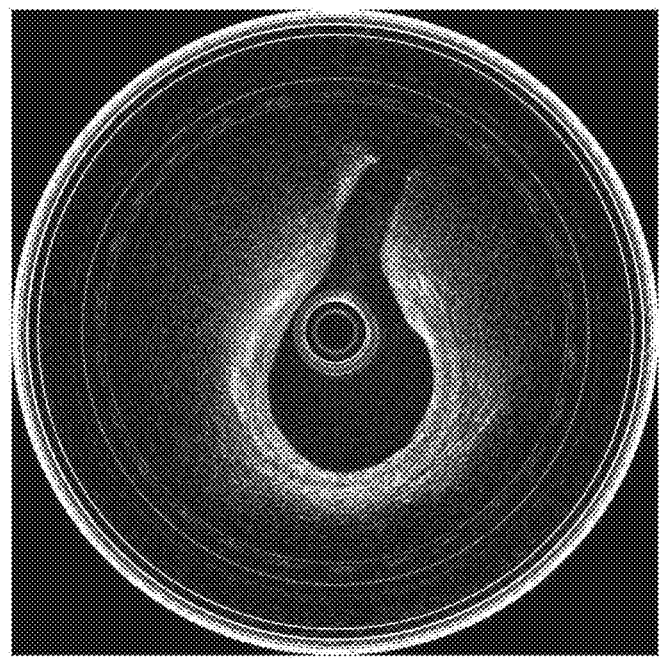
FIG. 12A and FIG. 12B show at least a further embodiment of an original image frame and a compensated image frame, respectively, in accordance with one or more aspects of the present disclosure.
Figure 12A:
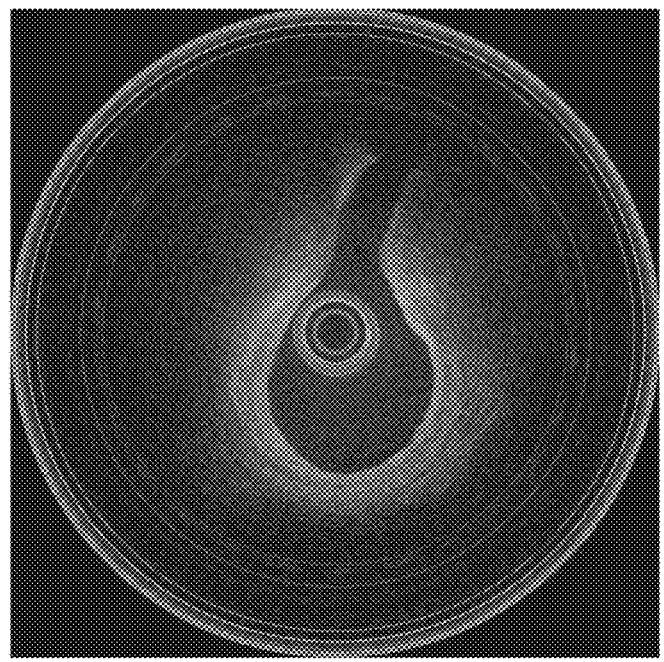

FIG. 12A and FIG. 12B show at least a further embodiment of an original image frame and a compensated image frame, respectively. FIGS. 12A and 12B show frame 613 of the conducted experiment.

Figure 13:
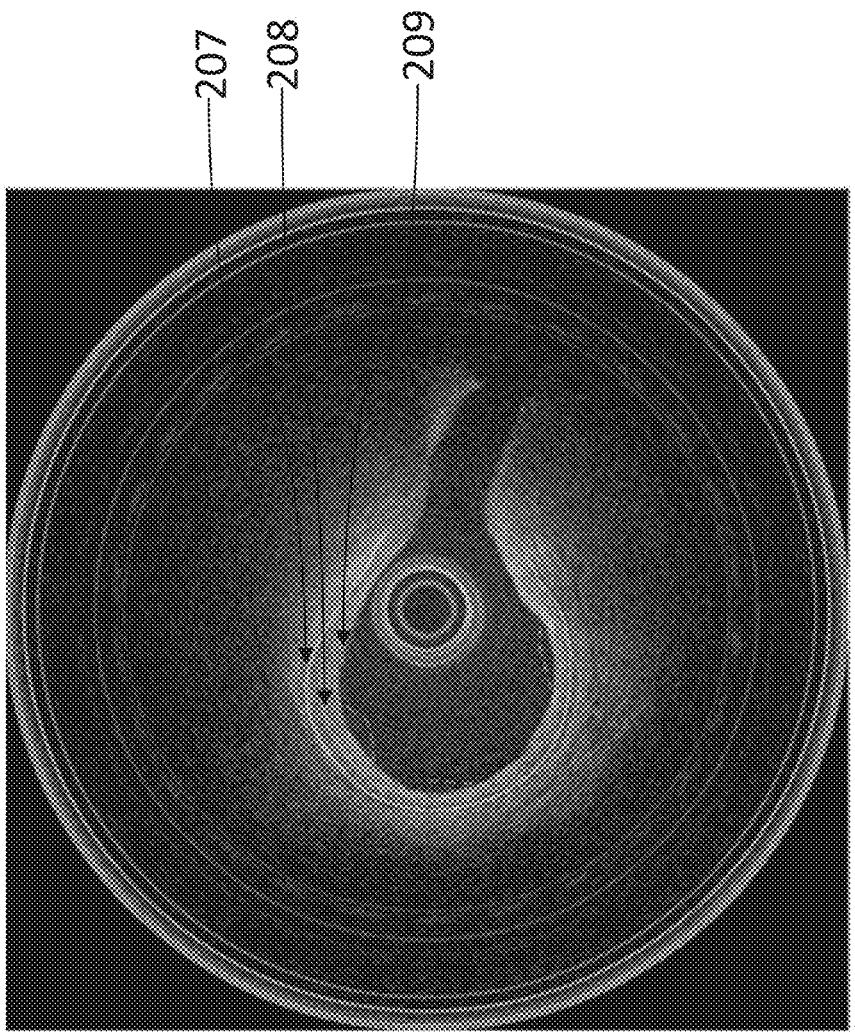
FIG. 13 shows at least one embodiment of using a ground truth data, data from the original image of FIG. 12A, and data from the compensated image of FIG. 12B as well as corresponding RMSE, max and min values in accordance with one or more aspects of the present disclosure.

FIG. 13 shows at least one embodiment of using a ground truth data (207 in FIG. 13), data from the original image (209 in FIG. 13) of FIG. 12A, and data from the compensated image (208 in FIG. 13) of FIG. 12B as well as corresponding RMSE, max, and min values. As shown in FIG. 13, the compensated data had an RMSE value of 0.104 mm, Max value of 0.201 mm, and Min value of $1.14 \times 10^{-3}$ mm. The original data had an RMSE value of 0.272 mm, a Max value of 0.612 mm, and a Min value of $1.39 \times 10^{-4}$ mm.

Figure 14:
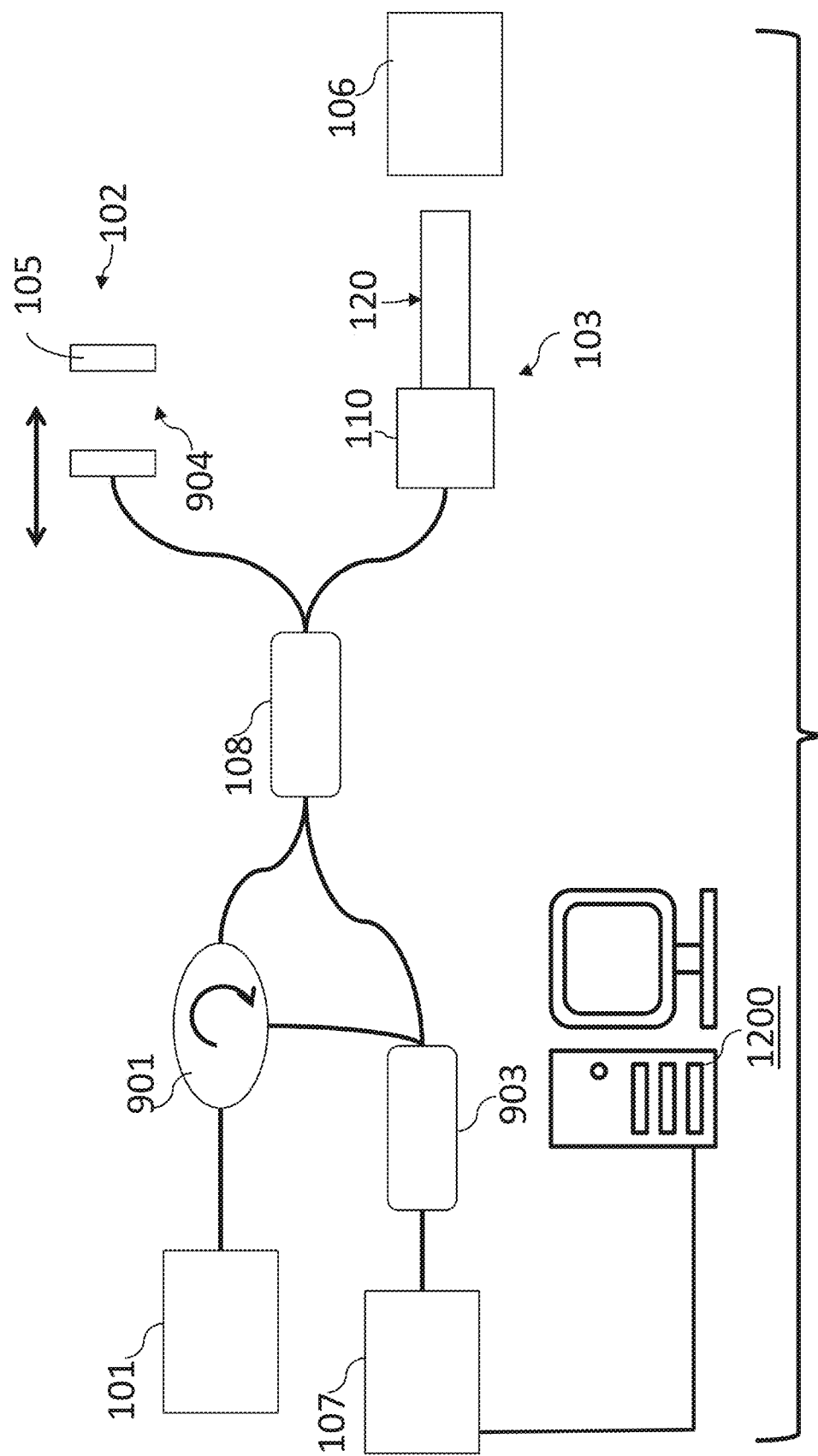
FIG. 14 shows at least one embodiment of an OCT apparatus or system for utilizing one or more imaging modalities that may be used to detect EEL in accordance with one or more aspects of the present disclosure.

In accordance with one or more further aspects of the present disclosure, bench top systems may be utilized with the EEL detection techniques disclosed herein. FIG. 14 shows an example of a system that can utilize the EEL detection techniques for a bench-top such as for ophthalmic applications. A light from a light source 101 delivers and splits into a reference arm 102 and a sample arm 103 with a deflecting (or deflection) section 108. A reference beam goes through a length adjustment section 904 (which is optional in one or more embodiments) and is reflected from a reference mirror (such as reference mirror or reference reflection 105 shown in FIG. 1A) in the reference arm 102 while a sample beam is reflected or scattered from a sample, target or object 106 in the sample arm 103 (e.g., via the PIU 110 and the catheter 120). In one embodiment, both beams combine at the deflecting/deflection section 108 and generate interference patterns. In one or more embodiments, the beams go to the combiner 903, and the combiner 903 combines both beams via the circulator 901 and the deflecting section 108. The combined beams preferably are delivered to one or more detectors (such as the one or more detectors 107). The output of the beam splitter (see e.g., beam splitter 104 in FIG. 1A), the deflecting section 108, and/or an interferometer is continuously acquired with one or more detectors, such as the one or more detectors 107. The electrical analog signals are converted to the digital signals to analyze them with a computer, such as, but not limited to, the computer 1200 (see FIGS. 1A-1B; also shown in FIGS. 14-17 discussed further below), the computer 1200' (see e.g., FIG. 18 discussed further below), etc.

Figure 15:
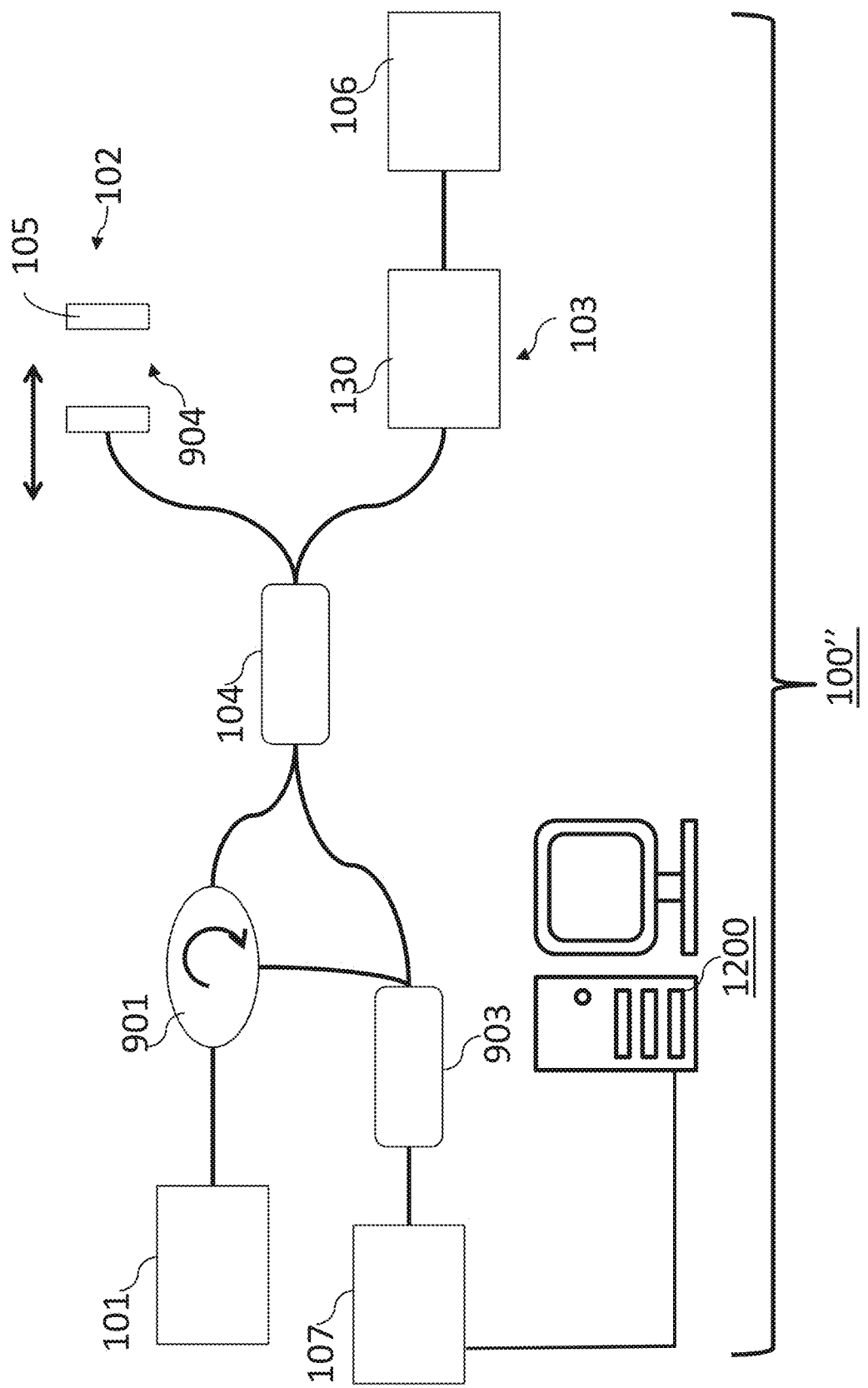
FIG. 15 shows at least another embodiment of an OCT apparatus or system for utilizing one or more imaging modalities that may be used to detect EEL in accordance with one or more aspects of the present disclosure.

In one or more embodiments, the sample arm 103 may include a phase shift unit 103 for a bench top system(s) as shown in system 100" in FIG. 15. The sample 106 may be located at the place of the mirror 105 used with the phase shift unit 130 (e.g., as shown in FIG. 1A). A light from a light source 101 delivers and splits into a reference arm 102 and a sample arm 103 with a splitter 104. A reference beam goes through a length adjustment section 904 and is reflected from a reference mirror (such as reference mirror 105 shown in FIGS. 14-16) in the reference arm 102 while a sample beam is reflected or scattered from a sample, target and/or object 106 through a phase shift unit (such as the phase shift unit 130) in the sample arm 103. In one embodiment, both beams combine at the splitter 104 and generate interference patterns. In one or more embodiments, the beams go to the combiner 903, and the combiner 903 combines both beams via the circulator 901 and the splitter 104, and the combined beams are delivered to one or more detectors (such as the one or more detectors 107). The output of the beam splitter 104 and/or an interferometer is continuously acquired with one or more detectors, such as the one or more detectors 107. The electrical analog signals are converted to the digital signals to analyze them with a computer.

There are many ways to compute EEL detection, rotation, intensity, or any other measurement discussed herein, and/or to control and/or manufacture an MMOCT device/apparatus, system and/or storage medium, digital as well as analog. In at least one embodiment, a computer, such as the console or computer 1200, 1200', may be dedicated to control and/or use OCT devices, systems, methods and/or storage mediums for use therewith described herein.

Figure 16:
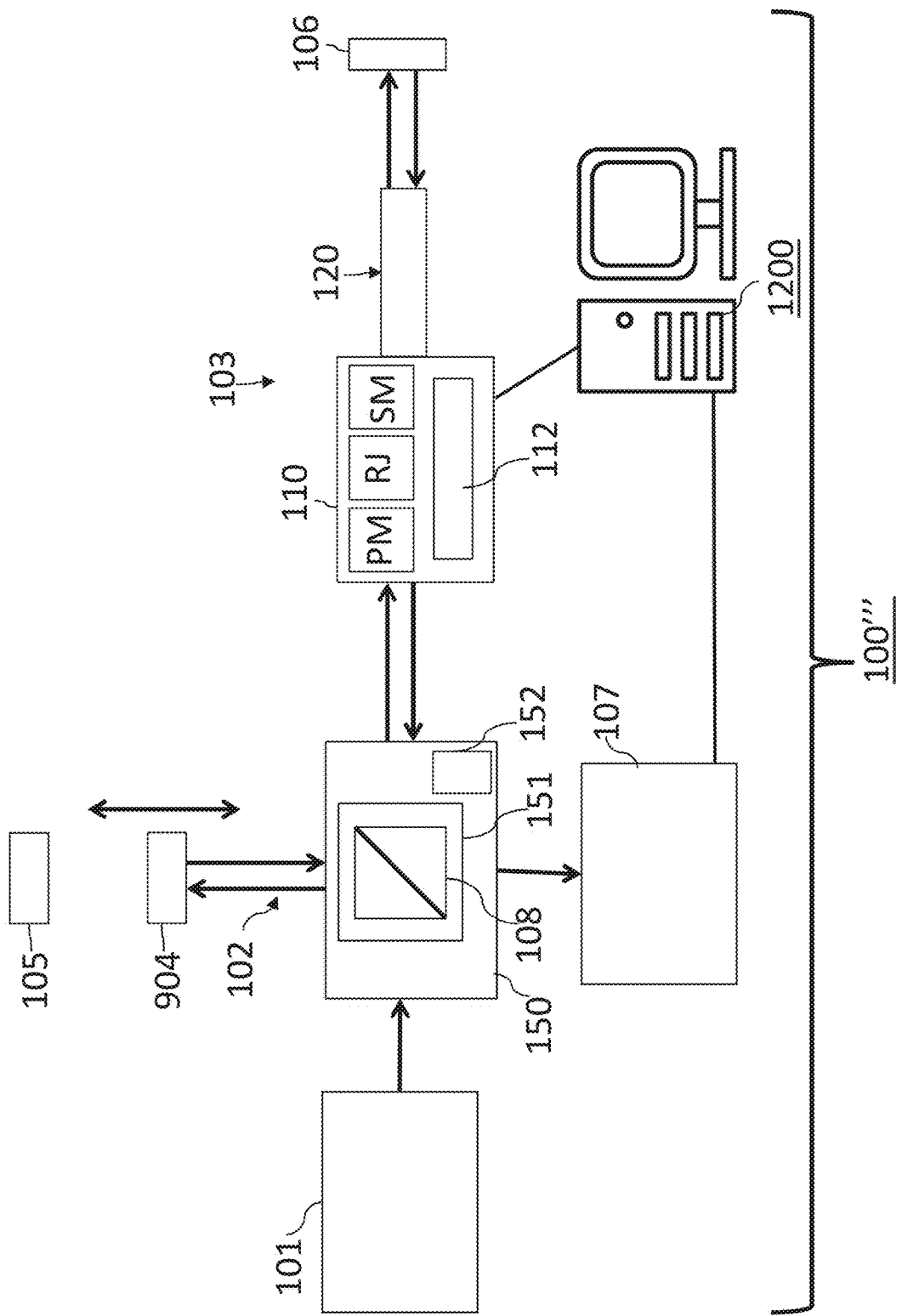
FIG. 16 shows at least a further embodiment of an OCT apparatus or system for utilizing one or more imaging modalities that may be used to detect EEL in accordance with one or more aspects of the present disclosure.

In accordance with one or more further aspects of the present disclosure, one or more other systems may be utilized with the lumen edge and artifact(s) detection OCT techniques disclosed herein. FIG. 16 shows an example of a system 100''' that may utilize the EEL detection techniques such as for ophthalmic applications. A light from a light source 101 delivers and splits into a reference arm 102 and a sample arm 103 with a deflecting section 108 (e.g., a beam splitter or other deflecting or deflected section discussed herein) located inside of an OCT imaging engine 150, which may also include an OCT interferometer 151 (which may house or include the deflecting section 108) and a swept source engine 152 in one or more embodiments. A reference beam may pass through a length adjustment section 904, which may operate to change the distance of a reference mirror (such as reference mirror or reference reflection 105; also shown in FIG. 1A) and is reflected from the reference reflection 105 in the reference arm 102 while a sample beam is reflected or scattered from a sample, target or object 106 in the sample arm 103. In one embodiment, both beams combine at the deflecting section 108 and generate interference patterns. In one or more embodiments, the combined beams are delivered to one or more detectors. The output of the interferometer 151 is continuously acquired with one or more detectors, such as the one or more detectors 107. The electrical analog signals are converted to the digital signals to analyze them with a computer, such as, but not limited to, the computer 1200 (see e.g., FIGS. 1A-1B; also shown in FIGS. 14-17 discussed further below), the computer 1200' (see e.g., FIG. 18 discussed further below), etc. In one or more embodiments, the sample arm 103 includes the PIU 110 and the catheter 120 so that the sample beam is reflected or scattered from the sample, target or object 106 as discussed herein. In one or more embodiments, the PIU 110 may include one or more motors to control the pullback operation of the catheter 120 (or one or more components thereof) and/or to control the rotation or spin of the catheter 120 (or one or more components thereof). For example, the PIU 110 may include a pullback motor (PM) and a spin motor (SM), and/or may include a motion control unit 112 that operates to perform the pullback and/or rotation features using the pullback motor PM and/or the spin motor SM. As discussed herein, the PIU 110 may include a rotary junction (e.g., rotary junction RJ as shown in FIG. 16). The rotary junction RJ may be connected to the spin motor SM so that the catheter 120 may obtain one or more views or images of the sample 106. The computer 1200 (or the computer 1200') may be used to control one or more of the pullback motor PM, the spin motor SM and/or the motion control unit 112. An OCT system may include one or more of the OCT engine 150, a computer (e.g., the computer 1200, the computer 1200', etc.), the PIU 110, the catheter 120, a monitor, etc. One or more embodiments of an OCT system may interact with one or more external systems, such as, but not limited to, an angio system, external displays, one or more hospital networks, external storage media, a power supply, a bedside controller (e.g., which may be connected to the OCT system using Bluetooth technology or other methods known for wireless communication), etc.

Unless otherwise discussed herein, like numerals indicate like elements. For example, while variations or differences exist between the systems, such as, but not limited to, the system 100, the system 100', the system 100'', the system 100''', etc. (e.g., differences between the position(s) of the reference reflection 105 (and/or reference arm 102) depending on the OCT system or method being used), one or more features thereof may be the same or similar to each other, such as, but not limited to, the light source 101, the deflecting section 108 or other component(s) thereof (e.g., the console 1200, the console 1200', etc.). Those skilled in the art will appreciate that the light source 101, the at least one detector 107 and/or one or more other elements of the system 100, may operate in the same or similar fashion to those like-numbered elements of one or more other systems, such as, but not limited to, the system 100', the system 100'', the system 100''', etc. as discussed herein. Those skilled in the art will appreciate that alternative embodiments of the system 100, the system 100', the system 100'', the system 100''', and/or one or more like-numbered elements of one of such systems, while having other variations as discussed herein, may operate in the same or similar fashion to the like-numbered elements of any of the other systems (or component(s) thereof) discussed herein. Indeed, while certain differences exist between the system 100, the system 100', the system 100" and the system 100''', as discussed herein, there are similarities between the systems discussed herein. Likewise, while the console or computer 1200 may be used in one or more systems (e.g., the system 100, the system 100', the system 100", the system 100''', etc.), one or more other consoles or computers, such as the console or computer 1200', may be used additionally or alternatively.

There are many ways to compute power and/or detect EEL, digital as well as analog. In at least one embodiment, a computer, such as the console or computer 1200, 1200', may be dedicated to the control and the monitoring of the OCT devices, systems, methods and/or storage mediums described herein.

The electric signals used for imaging may be sent to one or more processors, such as, but not limited to, a computer 1200 (see e.g., FIGS. 1A-1B and 14-17), a computer 1200' (see e.g., FIG. 18), etc. as discussed further below, via cable(s) or wire(s), such as, but not limited to, the cable(s) or wire(s) 113 (see FIG. 17).

Figure 17:
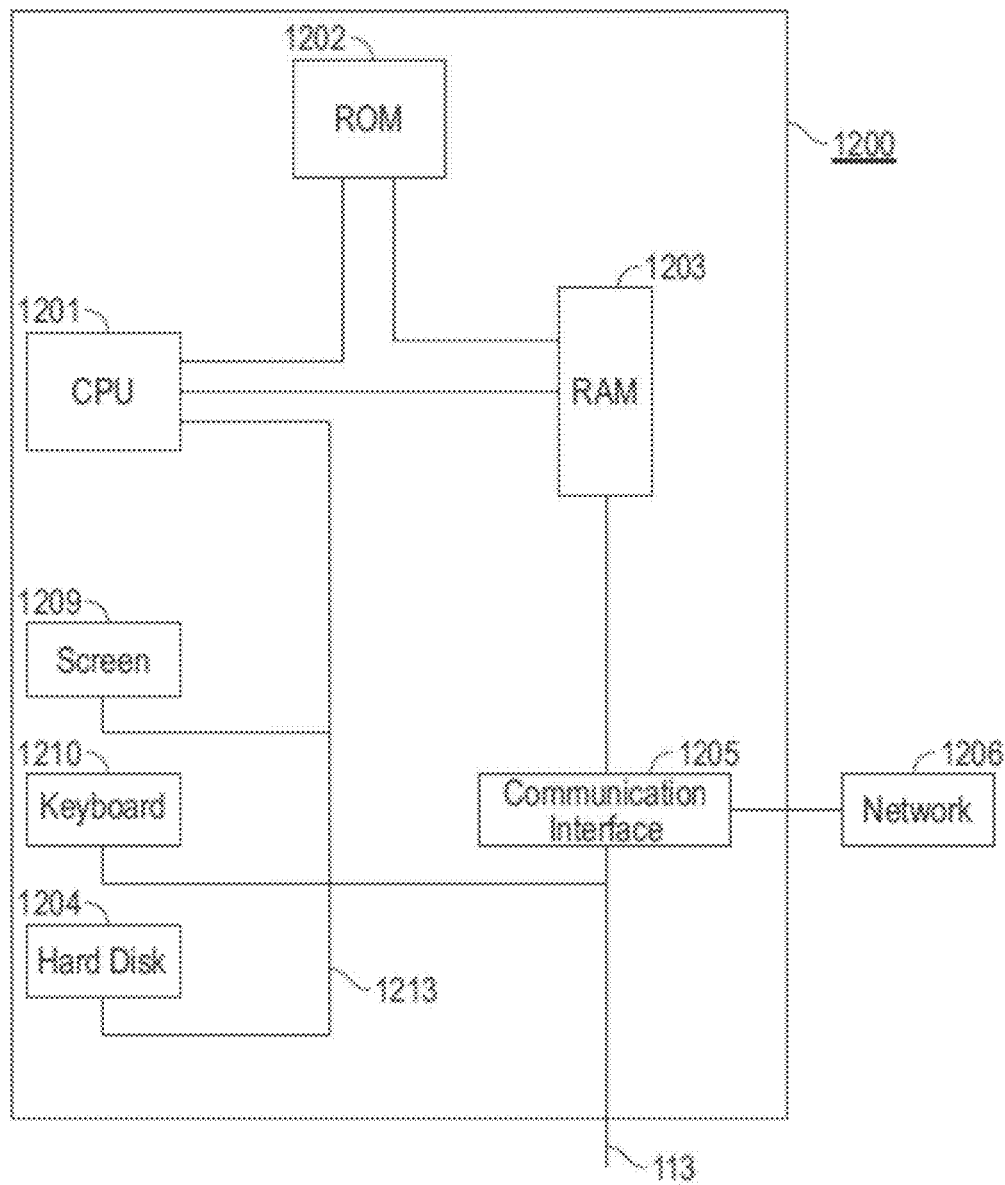
FIG. 17 shows a schematic diagram of an embodiment of a computer that may be used with one or more embodiments of an apparatus or system or one or more methods discussed herein in accordance with one or more aspects of the present disclosure.

Various components of a computer system 1200 (see e.g., the console or computer 1200 as shown in FIGS. 1A-1B and 14-17) are provided in FIG. 17. A computer system 1200 may include a central processing unit ("CPU") 1201, a ROM 1202, a RAM 1203, a communication interface 1205, a hard disk (and/or other storage device) 1204, a screen (or monitor interface) 1209, a keyboard (or input interface; may also include a mouse or other input device in addition to the keyboard) 1210 and a BUS or other connection lines (e.g., connection line 1213) between one or more of the aforementioned components (e.g., as shown in FIG. 17). In addition, the computer system 1200 may comprise one or more of the aforementioned components. For example, a computer system 1200 may include a CPU 1201, a RAM 1203, an input/output (I/O) interface (such as the communication interface 1205) and a bus (which may include one or more lines 1213 as a communication system between components of the computer system 1200; in one or more embodiments, the computer system 1200 and at least the CPU 1201 thereof may communicate with the one or more aforementioned components of a FORJ or a device or system using same, such as, but not limited to, the system 100, the system 100', the system 100" and/or the system 100''', discussed herein above, via one or more lines 1213), and one or more other computer systems 1200 may include one or more combinations of the other aforementioned components. The CPU 1201 is configured to read and perform computer-executable instructions stored in a storage medium. The computer-executable instructions may include those for the performance of the methods and/or calculations described herein. The computer system 1200 may include one or more additional processors in addition to CPU 1201, and such processors, including the CPU 1201, may be used for controlling and/or manufacturing a device, system or storage medium for use with same or for use with any lumen detection, stent(s) detection, and/or artifact(s) detection technique(s) discussed herein. The system 1200 may further include one or more processors connected via a network connection (e.g., via network 1206). The CPU 1201 and any additional processor being used by the system 1200 may be located in the same telecom network or in different telecom networks (e.g., performing, manufacturing, controlling and/or using technique(s) may be controlled remotely).

Figure 18:
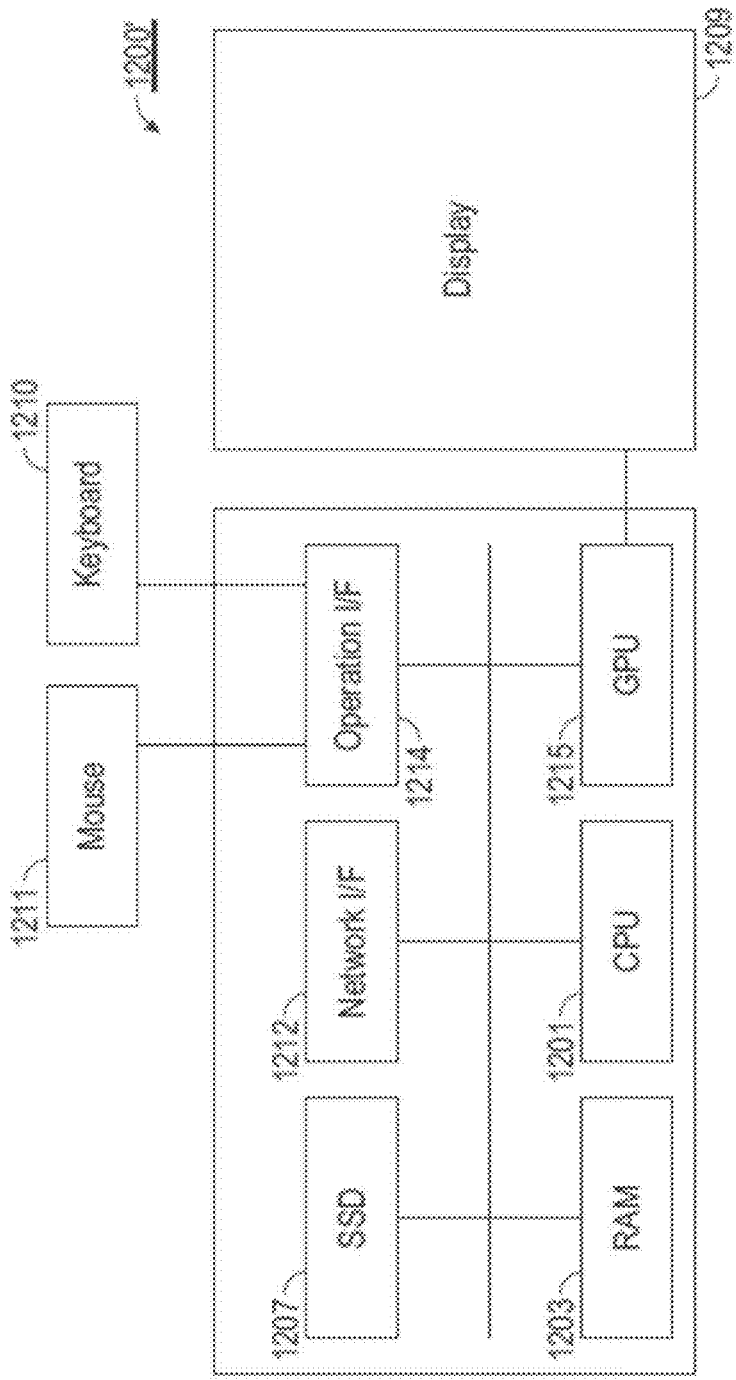
FIG. 18 shows a schematic diagram of another embodiment of a computer that may be used with one or more embodiments of an imaging apparatus or system or methods discussed herein in accordance with one or more aspects of the present disclosure.

The I/O or communication interface 1205 provides communication interfaces to input and output devices, which may include the light source 101, a RJ, a PM, an SM, unit 150, unit 112, a microphone, a communication cable and a network (either wired or wireless), a keyboard 1210, a mouse (see e.g., the mouse 1211 as shown in FIG. 18), a touch screen or screen 1209, a light pen and so on. The Monitor interface or screen 1209 provides communication interfaces thereto.

Any methods and/or data of the present disclosure, such as the methods for using and/or manufacturing a device, system or storage medium for use with same and/or method(s) for detecting EEL, lumen edge(s), stent(s), and/or artifact(s), including in OCT image(s), as discussed herein, may be stored on a computer-readable storage medium. A computer-readable and/or writable storage medium used commonly, such as, but not limited to, one or more of a hard disk (e.g., the hard disk 1204, a magnetic disk, etc.), a flash memory, a CD, an optical disc (e.g., a compact disc ("CD") a digital versatile disc ("DVD"), a Blu-Ray™ disc, etc.), a magneto-optical disk, a random-access memory ("RAM") (such as the RAM 1203), a DRAM, a read only memory ("ROM"), a storage of distributed computing systems, a memory card, or the like (e.g., other semiconductor memory, such as, but not limited to, a non-volatile memory card, a solid state drive (SSD) (see SSD 1207 in FIG. 18), SRAM, etc.), an optional combination thereof, a server/database, etc. may be used to cause a processor, such as, the processor or CPU 1201 of the aforementioned computer system 1200 to perform the steps of the methods disclosed herein. The computer-readable storage medium may be a non-transitory computer-readable medium, and/or the computer-readable medium may comprise all computer-readable media, with the sole exception being a transitory, propagating signal. The computer-readable storage medium may include media that store information for predetermined, limited, or short period(s) of time and/or only in the presence of power, such as, but not limited to Random Access Memory (RAM), register memory, processor cache(s), etc. Embodiment(s) of the present disclosure may also be realized by a computer of a system or apparatus that reads out and executes computer executable instructions (e.g., one or more programs) recorded on a storage medium (which may also be referred to more fully as a "non-transitory computer-readable storage medium") to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s).

In accordance with at least one aspect of the present disclosure, the methods, devices, systems, and computer-readable storage mediums related to the processors, such as, but not limited to, the processor of the aforementioned computer 1200, the processor of computer 1200', etc., as described above may be achieved utilizing suitable hardware, such as that illustrated in the figures. Functionality of one or more aspects of the present disclosure may be achieved utilizing suitable hardware, such as that illustrated in FIG. 17. Such hardware may be implemented utilizing any of the known technologies, such as standard digital circuitry, any of the known processors that are operable to execute software and/or firmware programs, one or more programmable digital devices or systems, such as programmable read only memories (PROMs), programmable array logic devices (PALs), etc. The CPU 1201 (as shown in FIG. 17 or FIG. 18) may also include and/or be made of one or more microprocessors, nanoprocessors, one or more graphics processing units ("GPUs"; also called a visual processing unit ("VPU")), one or more Field Programmable Gate Arrays ("FPGAs"), or other types of processing components (e.g., application specific integrated circuit(s) (ASIC)). Still further, the various aspects of the present disclosure may be implemented by way of software and/or firmware program(s) that may be stored on suitable storage medium (e.g., computer-readable storage medium, hard drive, etc.) or media (such as floppy disk(s), memory chip(s), etc.) for transportability and/or distribution. The computer may include a network of separate computers or separate processors to read out and execute the computer executable instructions. The computer executable instructions may be provided to the computer, for example, from a network or the storage medium.

As aforementioned, hardware structure of an alternative embodiment of a computer or console 1200' is shown in FIG. 18. The computer 1200' includes a central processing unit (CPU) 1201, a graphical processing unit (GPU) 1215, a random access memory (RAM) 1203, a network interface device 1212, an operation interface 1214 such as a universal serial bus (USB) and a memory such as a hard disk drive or a solid-state drive (SSD) 1207. Preferably, the computer or console 1200' includes a display 1209. The computer 1200' may connect with a rotary junction (e.g., RJ of FIG. 16, etc.), the motor PM, the motor SM, and/or one or more other components of a system (e.g., the system 100, the system 100', the system 100", the system 100''', etc.) via the operation interface 1214 or the network interface 1212. A computer, such as the computer 1200, 1200', may include the RJ, PM and/or the SM in one or more embodiments. The operation interface 1214 is connected with an operation unit such as a mouse device 1211, a keyboard 1210 or a touch panel device. The computer 1200' may include two or more of each component. Alternatively, the CPU 1201 or the GPU 1215 may be replaced by the field-programmable gate array (FPGA), the application-specific integrated circuit (ASIC) or other processing unit depending on the design of a computer, such as the computer 1200, the computer 1200', etc.

A computer program is stored in the SSD 1207, and the CPU 1201 loads the program onto the RAM 1203, and executes the instructions in the program to perform one or more processes described herein, as well as the basic input, output, calculation, memory writing and memory reading processes.

The computer, such as the computer 1200, 1200', communicates with the PIU 110, the rotary junction (e.g., the RJ, etc.), the motor PM, the motor SM, the catheter 120 and/or one or more other components of a system, such as the system 100, 100', 100", 100''', etc., to perform imaging, and reconstructs an image from the acquired intensity data. The monitor or display 1209 displays the reconstructed image, and may display other information about the imaging condition or about an object to be imaged. The monitor 1209 also provides a graphical user interface for a user to operate a system (e.g., the system 100, the system 100', the system 100", the system 100''', etc.), for example when performing OCT or other imaging technique, including, but not limited to, detection of EEL and/or lumen edge(s). An operation signal is input from the operation unit (e.g., such as, but not limited to, a mouse device 1211, a keyboard 1210, a touch panel device, etc.) into the operation interface 1214 in the computer 1200', and corresponding to the operation signal the computer 1200' instructs the system (e.g., the system 100, the system 100', the system 100", the system 100''', etc.) to set or change the imaging condition, and to start or end the imaging, and/or to start or end the lumen detection, stent(s) detection, and/or artifact(s) detection. The laser source 101 of an OCT system as aforementioned may have interfaces to communicate with the computers 1200, 1200' to send and receive the status information and the control signals.

Similarly, the present disclosure and/or one or more components of devices, systems and storage mediums, and/or methods, thereof also may be used in conjunction with optical coherence tomography probes. Such probes include, but are not limited to, the OCT imaging systems disclosed in U.S. Pat. Nos. 7,872,759; 8,289,522; and U.S. Pat. No. 8,928,889 to Tearney et al. and arrangements and methods of facilitating photoluminescence imaging, such as those disclosed in U.S. Pat. No. 7,889,348 to Tearney et al., as well as the disclosures directed to multimodality imaging disclosed in U.S. Pat. No. 9,332,942 and U.S. Patent Publication Nos. 2010/0092389, 2012/0101374, 2016/0228097, 2018/0045501 and 2018/0003481, each of which patents, patent publications and patent application(s) are incorporated by reference herein in their entireties. As aforementioned, any feature or aspect of the present disclosure may be used with OCT imaging systems, apparatuses, methods, storage mediums or other aspects or features as discussed in U.S. patent application Ser. No. 16/414,222, filed on May 16, 2019 and published on Dec. 12, 2019 as U.S. Pat. Pub. No. 2019/0374109, the entire disclosure of which is incorporated by reference herein in its entirety.

The present disclosure and/or one or more components of devices, systems and storage mediums, and/or methods, thereof also may be used in conjunction with arterial wall characterization (e.g., in OCT imaging), such as, but not limited to, the OCT imaging systems disclosed in U.S. Pat. Pub. No. 2020/0359911 A1, the entire disclosure of which is incorporated by reference herein in its entirety.

Although the disclosure herein has been described with reference to particular embodiments, it is to be understood that these embodiments are merely illustrative of the principles and applications of the present disclosure (and are not limited thereto). It is therefore to be understood that numerous modifications may be made to the illustrative embodiments and that other arrangements may be devised without departing from the spirit and scope of the present disclosure. The scope of the following claims is to be accorded the broadest interpretation so as to encompass all such modifications and equivalent structures and functions.

What is claimed is:

1. An imaging device for detecting external elastic lamina (EEL), the device comprising:
    one or more processors that operate to:
    calibrate a signal intensity of one or more imaging modalities to eliminate an effect of depth;
    detect a lumen;
    determine whether the lumen is located within a predetermined distance from a catheter or a portion of the catheter; and
    in a case where the lumen is located within the predetermined distance from the catheter or the portion of the catheter, (i) take a moving average of the signal intensity for a set or predetermined number of A-lines, (ii) find location(s) where a mean of the signal intensity changes abruptly by a set or predetermined amount, and (iii) detect a location of the EEL based on the detected abrupt changes or the detected change by the set or predetermined amount.

2. The imaging device of claim 1, wherein one or more of the following:
   (i) the predetermined distance from the catheter or the portion of the catheter is one or more of: within 3.0 mm, within 2.0 mm, within 1.0 mm-3.0 mm, a distance equal or less than a value of about 1.0 mm to about 3.0 mm, and/or a distance set by a user of the imaging device;
   (ii) the portion of the catheter is a center of the catheter, a side of the catheter, and/or a portion of the catheter set by a user of the imaging device;
   (iii) the predetermined or set number of A-lines is one or more of the following: 10 A-lines, 5 A-lines, 3 A-lines, 1-10 A-lines, 10 or more A-lines, 15 A-lines, and/or a number of A-lines set by a user of the imaging device; and/or
   (iv) the detected abrupt changes or the detected change by the set or predetermined amount includes one or more of the following: by 5 percent or more, by 10 percent or more, by 5-10% or more, a change from a low intensity to a high intensity, and/or an amount set or defined by the user.

3. The imaging device of claim 1, wherein the one or more processors further operate to check whether the smoothened EEL is continuous in a Cartesian coordinate and/or a polar coordinate except side branch location(s) in or near the lumen or plaque location(s) in or near the lumen.

4. The imaging device of claim 1, wherein the one or more processors further operate to automatically detect EEL and to:
   in a case where the lumen is not located within the predetermined distance from the catheter or the portion of the catheter, indicate that no EEL is detected, or
   in the case where the lumen is located within the predetermined distance from the catheter or the portion of the catheter, then: determine whether the EEL is located within a predetermined distance from the lumen, and, in a case where the EEL is located within the predetermined distance from the lumen, interpolate between detected points, perform smoothening on the EEL, and check whether the smoothened EEL is continuous in a Cartesian coordinate and/or a polar coordinate, or, in a case where the EEL is not located within the predetermined distance from the lumen, then determine whether plaque exists, and, in a case where plaque exists, then performing processing on an EEL pre neighborhood curvature image or frame to obtain an EEL neighborhood curvature image or frame having a complete EEL and then interpolating from nearby detection results, interpolating between detected points, performing smoothening on the EEL, and checking whether the smoothened EEL is continuous in a Cartesian coordinate and/or a polar coordinate, or, in a case where the plaque does not exist, then interpolate from nearby detection results, interpolate between detected points, perform smoothening on the EEL, and check whether the smoothened EEL is continuous in a Cartesian coordinate and/or a polar coordinate.

5. The imaging device of claim 4, wherein one or more of the following:
   (i) the predetermined distance from the catheter or the portion of the catheter is one or more of: within 3.0 mm, within 2.0 mm, within 1.0 mm-3.0 mm, and/or a distance equal or less than a value of about 1.0 mm to about 3.0 mm;
   (ii) the portion of the catheter is a center of the catheter, a side of the catheter, and/or a portion of the catheter set by a user of the imaging device;
   (iii) the predetermined or set number of A-lines is one or more of the following: 10 A-lines, 5 A-lines, 3 A-lines, 1-10 A-lines, 10 or more A-lines, 15 A-lines, and/or a number of A-lines set by a user of the imaging device;
   (iv) the detected abrupt changes or the detected change by the set or predetermined amount includes one or more of the following: by 5 percent or more, by 10 percent or more, by 5-10% or more, a change from a low intensity to a high intensity, and/or an amount set or defined by the user; and/or
   (v) the predetermined distance of the detected EEL location to or from the lumen is one or more of the following: within 1 mm, within 2 mm, within 1-2 mm, a distance equal or less than a value of about 1.0 mm to about 3.0 mm, and/or within a distance set by a user of the imaging device.

6. The imaging device of claim 5, wherein the one or more processors further operate to check whether the smoothened EEL is continuous in the Cartesian coordinate and/or the polar coordinate except side branch location(s) or plaque location(s).

7. The imaging device of claim 1, wherein the one or more processors further operate to:
   detect a lumen edge in one or more intravascular images;
   determine one or more reference frames;
   determine whether the EEL is seen in the one or more reference frames;
   detect the EEL;
   measure a diameter of the EEL; and
   determine a size and shape of a stent to be used in the lumen.

8. A method for detecting external elastic lamina (EEL), the method comprising:
   calibrating a signal intensity of one or more imaging modalities to eliminate an effect of depth;
   detecting a lumen;
   determining whether the lumen is located within a predetermined distance from a catheter or a portion of the catheter; and
   in a case where the lumen is located within the predetermined distance from the catheter or the portion of the catheter, (i) taking a moving average of the signal intensity for a set or predetermined number of A-lines, (ii) finding location(s) where a mean of the signal intensity changes abruptly by a set or predetermined amount, and (iii) detecting a location of the EEL based on the detected abrupt changes or the detected change by the set or predetermined amount.

9. The method of claim 8, further comprising:
   determining whether the EEL is located within a predetermined distance from the lumen, and
   in a case where the EEL is located within the predetermined distance from the lumen, interpolating between the detected points, performing smoothening on the EEL, and checking whether the smoothened EEL is continuous in a Cartesian coordinate and/or a polar coordinate.

10. The method of claim 9, wherein one or more of the following:
   the predetermined distance of the detected EEL location to or from the lumen is one or more of the following:

within 1 mm, within 2 mm, within 1-2 mm, a distance equal or less than a value of about 1.0 mm to about 3.0 mm, and/or within a distance set by a user of the imaging device; and/or the checking step checks whether the smoothened EEL is continuous in the Cartesian coordinate and/or the polar coordinate except side branch location(s) in or near the lumen or plaque location(s) in or near the lumen.

11. The method of claim 9, further comprising:

in a case where the EEL is not located within the predetermined distance from the lumen, determining whether plaque exists; and in a case where plaque exists, then performing processing on an EEL pre neighborhood curvature image or frame to obtain an EEL neighborhood curvature image or frame having a complete EEL and then interpolating from nearby detection results, interpolating between detected points, performing smoothening on the EEL, and checking whether the smoothened EEL is continuous in a Cartesian coordinate and/or a polar coordinate, or, in a case where the plaque does not exist, then interpolating from nearby detection results, interpolating between detected points, performing smoothening on the EEL, and checking whether the smoothened EEL is continuous in a Cartesian coordinate and/or a polar coordinate.

12. The method of claim 11, wherein the checking step checks whether the smoothened EEL is continuous in the Cartesian coordinate and/or the polar coordinate except side branch location(s) in or near the lumen or plaque location(s) in or near the lumen.

13. The method of claim 8, wherein one or more of the following:

(i) the predetermined distance from the catheter or the portion of the catheter is one or more of: within 3.0 mm, within 2.0 mm, within 1.0 mm-3.0 mm, and/or a distance equal or less than a value of about 1.0 mm to about 3.0 mm;

(ii) the portion of the catheter is a center of the catheter, a side of the catheter, and/or a portion of the catheter set by a user of the imaging device;

(iii) the predetermined or set number of A-lines is one or more of the following: 10 A-lines, 5 A-lines, 3 A-lines, 1-10 A-lines, 10 or more A-lines, 15 A-lines, and/or a number of A-lines set by a user of the imaging device; and/or (iv) the detected abrupt changes or the detected change by the set or predetermined amount includes one or more of the following: by 5 percent or more, by 10 percent or more, by 5-10% or more, a change from a low intensity to a high intensity, and/or an amount set or defined by the user.

14. The method of claim 8, further comprising:

detecting a lumen edge in one or more intravascular images;

determining one or more reference frames;

determining whether the EEL is seen in the one or more reference frames;

detecting the EEL;

measuring a diameter of the EEL; and determining a size and shape of a stent to be used in the lumen.

15. The method of claim 14, further comprising one or more of the following:

in a case where the EEL is not seen in the reference frame, determining whether the EEL is seen in one or more of the following: a nearby frame, a frame before or after the reference frame, a couple or a few frames away from the reference frame, and/or a frame near to the reference frame;

in a case where the EEL is not seen in one or more of the following: a nearby frame, a frame before or after the reference frame, a couple or a few frames away from the reference frame, and/or a frame near to the reference frame, measuring the diameter of the lumen and determining the size and the shape of the stent;

in a case where the EEL is seen in one or more of the following: a nearby frame, a frame before or after the reference frame, a few frames away from the reference frame, and/or a frame near to the reference frame, determining whether to change the reference frame to one or more of the following: the nearby frame, the frame before or after the reference frame, a couple or a few frames away from the reference frame, and/or the frame near to the reference frame;

in a case where it is determined to change the reference frame to one or more of the following: the nearby frame, the frame before or after the reference frame, a couple or a few frames away from the reference frame, and/or the frame near to the reference frame, detecting the EEL, measuring the diameter of the EEL, and determining the size and shape of the stent; and/or in a case where it is determined to not change the reference frame to one or more of the following: the nearby frame, the frame before or after the reference frame, a couple or a few frames away from the reference frame, and/or the frame near to the reference frame, measuring the diameter of the lumen and determining the size and the shape of the stent.

16. The method of claim 15, further comprising one or more of the following: issuing a warning on a display in a case where a reference frame is not appropriate or should be changed; and/or issuing a warning on a display in a case where a reference frame is not appropriate or should be changed based on the EEL detection.

17. The method of claim 14, wherein the size and shape of the stent includes one or more of the following: a diameter and a length of the stent, a circumference of the stent, and/or a volume of the stent; and the imaging device aids a user of the imaging device to select the size and/or shape of the stent.

18. The method of claim 14, further comprising displaying a graphical user interface (GUI) on a display, wherein one or more of the following: a user of the display and/or the GUI modifies the location of the EEL, and/or the GUI includes a button and/or guidance to navigate the user.

19. The method of claim 14, further comprising compensating a signal intensity reduction due to a depth and analyzing the compensated intensity such that one or more features being imaged are located relatively deeper than a surface or the edge of the lumen.

20. A non-transitory computer-readable storage medium storing at least one program for causing a computer to execute a method for detecting external elastic lamina (EEL), the method comprising:

calibrating a signal intensity of one or more imaging modalities to eliminate an effect of depth;

detecting a lumen;

determining whether the lumen is located within a predetermined distance from a catheter or a portion of the catheter; and in a case where the lumen is located within the predetermined distance from the catheter or the portion of the catheter, (i) taking a moving average of the signal intensity for a set or predetermined number of A-lines, (ii) finding location(s) where a mean of the signal intensity changes abruptly by a set or predetermined amount, and (iii) detecting a location of the EEL based on the detected abrupt changes or the detected change by the set or predetermined amount.

* * * * *